United States Patent
Fujimaru et al.

(10) Patent No.: US 8,822,373 B2
(45) Date of Patent: Sep. 2, 2014

(54) PARTICULATE WATER ABSORBING AGENT AND PRODUCTION METHOD THEREOF

(75) Inventors: Hirotama Fujimaru, Himeji (JP); Eri Nagasawa, Himeji (JP); Masatoshi Nakamura, Himeji (JP); Hiroyuki Ikeuchi, Himeji (JP); Makoto Nagasawa, Nara (JP); Ryoko Tahara, Kitaibaraki (JP)

(73) Assignee: Nippon Shokubai Co., Ltd, Osaka (JP)

( * ) Notice: Subject to any disclaimer, the term of this patent is extended or adjusted under 35 U.S.C. 154(b) by 37 days.

(21) Appl. No.: 12/307,922

(22) PCT Filed: Aug. 30, 2007

(86) PCT No.: PCT/JP2007/067348
§ 371 (c)(1),
(2), (4) Date: Jan. 7, 2009

(87) PCT Pub. No.: WO2008/026772
PCT Pub. Date: Mar. 6, 2008

(65) Prior Publication Data
US 2009/0312183 A1     Dec. 17, 2009

(30) Foreign Application Priority Data

Aug. 31, 2006 (JP) ................. 2006-235692
Mar. 19, 2007 (JP) ................. 2007-071075

(51) Int. Cl.
| | |
|---|---|
| *B01J 20/26* | (2006.01) |
| *B01J 20/30* | (2006.01) |
| *A61L 15/24* | (2006.01) |
| *A61L 15/60* | (2006.01) |
| *C08F 120/06* | (2006.01) |
| *C08F 220/06* | (2006.01) |
| *A61F 13/53* | (2006.01) |

(52) U.S. Cl.
CPC .............. *A61L 15/60* (2013.01); *A61L 15/24* (2013.01); *C08F 120/06* (2013.01); *C08F 220/06* (2013.01); *A61F 2013/530481* (2013.01)
USPC ............ 502/402; 502/400; 502/401

(58) Field of Classification Search
USPC .......................... 502/400, 401, 402
See application file for complete search history.

(56) References Cited

U.S. PATENT DOCUMENTS

| | | | |
|---|---|---|---|
| 5,610,208 A | 3/1997 | Dairoku et al. | |
| 6,080,425 A * | 6/2000 | Miljkovic et al. | ............. 424/450 |

(Continued)

FOREIGN PATENT DOCUMENTS

| | | |
|---|---|---|
| CN | 1747752 A | 3/2006 |
| EP | 0856528 A1 | 8/1998 |

(Continued)

OTHER PUBLICATIONS

Database WPI Week 200130, Thomson Scientific, London, GB, AN, 2001-284977, XP-002566831, 2001, 3 pages.

(Continued)

*Primary Examiner* — Stanley Silverman
*Assistant Examiner* — Daniel Berns
(74) *Attorney, Agent, or Firm* — Morrison & Foerster LLP

(57) ABSTRACT

A particulate water absorbing agent includes a polyacrylic acid and/or a salt thereof water absorbent resin as a main component, wherein the water absorbent resin includes $\alpha$-hydroxycarboxylic acid and/or a salt thereof, and the absorbing agent satisfies a specific particle size distribution and a specific water absorbing performance, thereby solving the conventional problems. Further, a production method of the water absorbing agent is characterized in that $\alpha$-hydroxycarboxylic acid and/or a salt thereof is added to (a) a monomer aqueous solution whose main component is acrylic acid and/or a salt thereof and which is being cross-linked and polymerized or (b) a hydrogel polymer after the polymerization. As a result, in the particulate water absorbing agent containing the water absorbent resin as a main component, it is possible to realize both excellent water absorbing performance and excellent coloring prevention effect. Further, it is possible to provide an absorbing article particulate water absorbing agent which is suitable for practical use.

21 Claims, 1 Drawing Sheet

(56) References Cited

U.S. PATENT DOCUMENTS

| | | |
|---|---|---|
| 6,444,744 B1 | 9/2002 | Fujimaru et al. |
| 6,448,320 B1 | 9/2002 | Igarashi et al. |
| 2002/0013394 A1 | 1/2002 | Dairoku et al. |
| 2003/0092849 A1* | 5/2003 | Dairoku et al. ............ 525/329.7 |
| 2004/0110914 A1* | 6/2004 | Nakahara et al. .......... 526/317.1 |
| 2005/0013865 A1 | 1/2005 | Nestler et al. |
| 2005/0085604 A1 | 4/2005 | Handa et al. |
| 2006/0025536 A1 | 2/2006 | Dairoku et al. |
| 2006/0204755 A1 | 9/2006 | Torii et al. |
| 2008/0032888 A1 | 2/2008 | Nakamura et al. |

FOREIGN PATENT DOCUMENTS

| | | |
|---|---|---|
| EP | 1466928 A1 | 10/2004 |
| JP | 04-331205 A | 11/1992 |
| JP | 05-086251 A | 4/1993 |
| JP | 7-278225 A | 10/1995 |
| JP | 7-310021 A | 11/1995 |
| JP | 10-273602 A | 10/1998 |
| JP | 2000-327926 A | 11/2000 |
| JP | 2003-052742 A | 2/2003 |
| JP | 2003-206381 A | 7/2003 |
| JP | 2005-186016 A | 7/2005 |
| JP | 2005-344103 A | 12/2005 |
| WO | WO-00/55245 A1 | 9/2000 |
| WO | 2005/012369 A1 | 2/2005 |
| WO | WO 2007/072969 * | 6/2007 ............ C08L 101/08 |

OTHER PUBLICATIONS

Database WPI Week 200351, Thomson Scientific, London, GB, AN, 2003-536080, XP-002562078, 2003, 5 pages.
Database WPI Week 200554, Thomson Scientific, London, GB, AN 2005-524779, XP-002566830, 2005, 2 pages.
Extended European Search Report received for EP Patent Application No. 07806790.7, mailed on Feb. 15, 2010, 7 pages.
International Search Report mailed Nov. 27, 2007, for PCT Application No. PCT/JP2007/067348 filed Aug. 30, 2007, 3 pages.
International Written Opinion mailed Nov. 27, 2007, for PCT Application No. PCT/JP2007/067348 filed Aug. 30, 2007, 4 pages.
Office Action received for Chinese Patent Application No. 200780030045.1, mailed on Sep. 16, 2010, 17 pages (9 pages of English Translation and 8 pages of office Action).
Office Action received for Japanese Patent Application No. 2009-505673, mailed on Nov. 12, 2013, 4 pages (3 pages of English Translation and 1 page of Office Action).

* cited by examiner

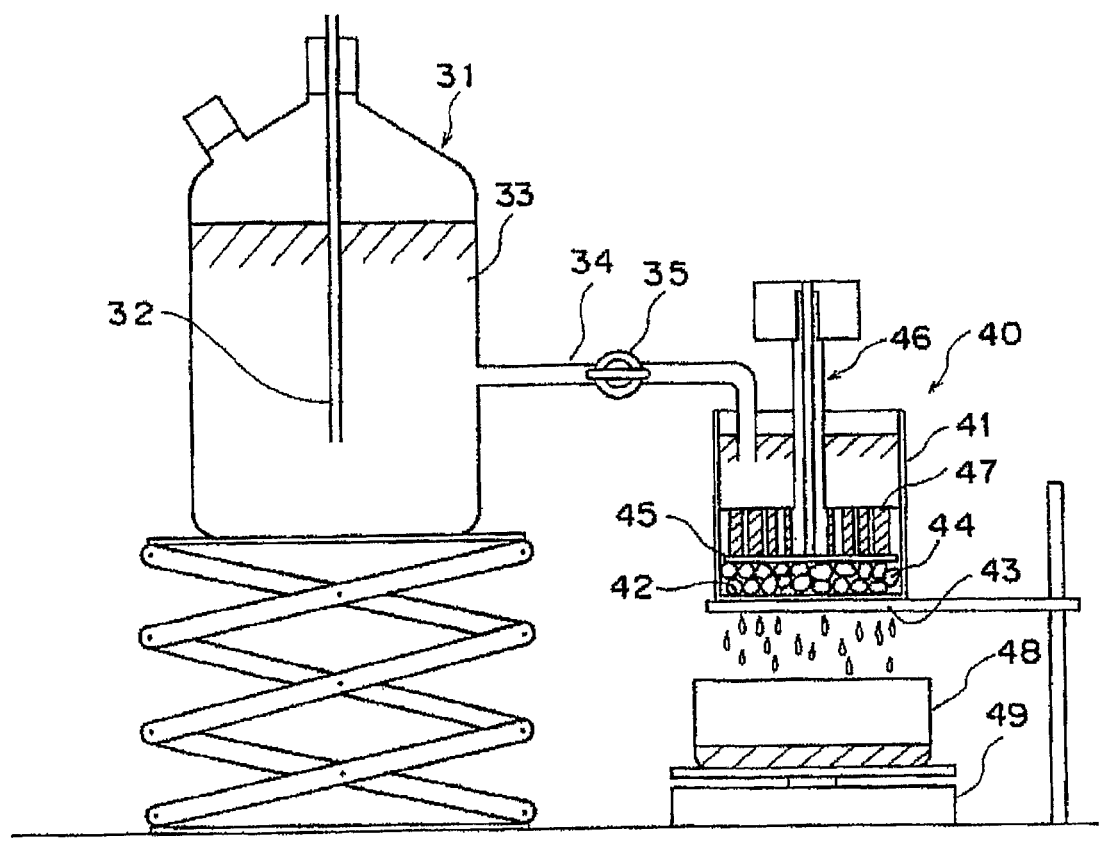

PARTICULATE WATER ABSORBING AGENT AND PRODUCTION METHOD THEREOF

CROSS REFERENCE TO RELATED APPLICATIONS

This is a U.S. National Phase application of PCT/JP2007/067348, filed Aug. 30, 2007, which claims priority to Japanese Application No. 2006-235692, filed Aug. 31, 2006, and Japanese Application No. 2007-071075, filed Mar. 19, 2007, all of which are hereby incorporated by reference in the present disclosure in their entirety.

TECHNICAL FIELD

The present invention relates to a particulate water absorbing agent containing a polyacrylic acid and/or a salt thereof water absorbent resin as a main component and a production method thereof. More specifically, the present invention relates to (i) a particulate water absorbing agent which is substantially white and free from any problem such as coloring with time passage and which has high properties and excellent safety and (ii) a production method thereof.

BACKGROUND ART

Recently, a water absorbent resin having high absorbency has been developed and is widely used mainly for a disposable purpose, e.g., as an absorbing article such as a disposable diaper and a sanitary napkin, further, as an agriculture/horticulture water retaining agent, an industrial waterproofing agent, and the like. As a material for the water absorbent resin, a large number of monomers and a large amount of hydrophilic polymers have been proposed. Particularly, it is most general that polyacrylic acid and/or a salt thereof water absorbent resin using acrylic acid and/or salt thereof as a monomer is industrially used due to its high water absorbing performance.

As water absorbent properties conventionally desired in the water absorbent resin, there are known a large number of properties (parameters) such as an absorbency without pressure, an absorbency against pressure, a water absorbing rate, a permeability potential without pressure, a permeability potential against pressure, an impact resistance, a anti-urine property, a fluidity, a gel strength, a particle size, and the like, and there have been proposed various definitions (parameter measurement methods) adopted to each property (for example, the absorbency without pressure) from various view points.

These water absorbent resins are used mainly for sanitary materials such as a diaper and a sanitary napkin. Thus, the water absorbent resin is required to be white at the time of shipment from the industry so as not to give a user visually uncomfortable feeling due to coloring in case where powdery water absorbent resin is combined with white pulp in a sanitary material. Further, the water absorbent resin is generally white powder, and it is known that the water absorbent resin is colored (from yellow to brown) with time passage, even after the shipment, during reservation or transport thereof, further, in being used for a sanitary material, so that the water absorbent resin is also required to be white in case where the absorbing article is reserved for an extended period of time.

In order to solve the coloring problem of the water absorbent resin, there were proposed: a method in which acrylic acid monomer and/or salt thereof is polymerized with hydroxyperoxide by a reducing agent and then the polymerized resultant is treated with a silane coupling agent (Patent Document 1); a method in which a water absorbent resin is treated with an organic phosphoric acid compound or salt thereof (Patent Document 2); a method in which a total amount of hydroquinone and benzoquinone in acrylic acid is controlled so as to be 0.2 ppm or less (Patent Document 3); a method in which an inorganic reducing agent is added to a water absorbent resin (Patent Document 4); a method in which organic carboxylic acid or salt thereof is added to a water absorbent resin (Patent Documents 5, 6, and 7); a method in which tocopherol is used as a polymerization inhibitor of acrylic acid so as to carry out polymerization (Patent Document 8); and a method in which a metallic chelating agent is added in producing a water absorbent resin (Patent Documents 9 and 10).

However, each of the foregoing methods results in insufficient improvement in the coloring problem, lower properties, higher cost, and raises a problem in safety depending on a compound to be used.

[Patent Document 1]
Japanese Unexamined Patent Publication No. 331205/1992 (Tokukaihei 4-331205 (Publication date: Nov. 19, 1992))
[Patent Document 2]
Japanese Unexamined Patent Publication No. 86251/1993 (Tokukaihei 5-86251 (Publication date: Apr. 6, 1993))
[Patent Document 3]
U.S. Pat. No. 6,444,744 (Publication date: Sep. 3, 2002)
[Patent Document 4]
International Publication WO2000/55245 (Publication date: Sep. 21, 2000)
[Patent Document 5]
Japanese Unexamined Patent Publication No. 327926/2000 (Tokukai 2000-327926 (Publication date: Nov. 28, 2000))
[Patent Document 6]
Japanese Unexamined Patent Publication No. 52742/2003 (Tokukai 2003-52742 (Publication date: Feb. 25, 2003))
[Patent Document 7]
Japanese Unexamined Patent Publication No. 186016/2005 (Tokukai 2005-186016 (Publication date: Jul. 14, 2005))
[Patent Document 8]
International Publication WO2003/53482 (Publication date: Jul. 3, 2003)
[Patent Document 9]
Japanese Unexamined Patent Publication No. 206305/2003 (Tokukai 2003-206305 (Publication date: Jul. 22, 2003))
[Patent Document 10]
Japanese Unexamined Patent Publication No. 206381/2003 (Tokukai 2003-206381 (Publication date: Jul. 22, 2003))

DISCLOSURE OF INVENTION

An object to be achieved by the present invention is to realize both excellent water absorbing ability and excellent coloring prevention effect, which are opposite to each other, in a particulate water absorbing agent containing a water absorbent resin as a main component.

The inventors of the present invention diligently studied so as to achieve the foregoing object. As a result, they found it possible to achieve the foregoing object by adopting the following arrangement, thereby completing the present invention.

A particulate water absorbing agent of the present invention comprising a polyacrylic acid and/or a salt thereof water absorbent resin as a main component, wherein the water absorbent resin internally includes α-hydroxycarboxylic acid and/or a salt thereof and satisfies at least one of the following conditions, (a) an amount of particles whose particle diameter is less than 150 μm ranges from 0 to 5 mass %, and a mass average particle diameter (D50) ranges from 200 to 600 μm, and a particle size distribution logarithmic standard deviation (σζ) ranges from 0.20 to 0.40.

(b) an absorbency against pressure (AAP) of the water absorbent resin with respect to 0.90 mass % of sodium chloride aqueous solution for 60 minutes is at least 15 g/g where the pressure is 4.8 kPa, and (c) a saline flow conductivity (SFC) is at least $5(\times 10^{-7} \cdot cm^3 \cdot s \cdot g^{-1})$ where the saline is 0.69 mass % of sodium chloride aqueous solution.

A method of the present invention for producing a particulate water absorbing agent including a polyacrylic acid and/or a salt thereof water absorbent resin as a main component, said method comprising the steps of: cross-linking and polymerizing a monomer solution containing acrylic acid and/or a salt thereof as a main component; and drying a hydrogel polymer obtained by the polymerization, wherein the polymerization is carried out in the presence of α-hydroxycarboxylic acid and/or a salt thereof.

A method of the present invention for producing a particulate water absorbent resin including a polyacrylic acid and/or a salt thereof water absorbent resin as a main component, said method comprising the steps of: cross-linking and polymerizing a monomer solution containing acrylic acid and/or a salt thereof as a main component; and drying a hydrogel obtained by the polymerization, wherein α-hydroxycarboxylic acid and/or a salt thereof is added to the hydrogel cross-linked polymer after the polymerization.

Additional objects, features, and strengths of the present invention will be made clear by the description below. Further, the advantages of the present invention will be evident from the following explanation in reference to the drawings.

BRIEF DESCRIPTION OF DRAWING

FIG. 1 is a schematic illustrating an SFC measuring device.

REFERENCE NUMERALS

31 Tank
32 Glass tube
33 0.69 mass % physiological saline
34 L-shaped tube with a cock
35 Cock
40 Container
41 Cell
42 Stainless metal gauze
43 Stainless metal gauze
44 Swollen gel
45 Glass filter
46 Piston
47 Hole
48 Collecting container
49 Even balance

BEST MODE FOR CARRYING OUT THE INVENTION

The following further details the present invention, but the present invention is not limited to descriptions of the following embodiments, but may be altered by a skilled person within the scope of the claims. An embodiment based on a proper combination of technical means disclosed in different embodiments is encompassed in the technical scope of the present invention. Note that, in the present specification, "mass" is a synonymous of "weight". Further, "particle size" is synonymous of "particle diameter".

(1) Water Absorbent Resin

The water absorbent resin of the present embodiment is a water-swelling and water-insoluble polymer obtained by introducing a cross-linking structure into a polymer. The water-swelling means a state in which a centrifuge retention capacity (CRC) with respect to physiological saline is 2 g/g or more, preferably 5 to 200 g/g, more preferably 20 to 100 g/g. Further, the water-insoluble means such a substantially water-insoluble property that an amount of a water-soluble content in the resin is essentially 0 to 50 mass % or less, preferably 0 to 25 mass %, more preferably 0 to 15 mass %, still more preferably 0 to 10 mass %. Note that, a measuring method thereof will be defined in below-described Examples.

The water absorbent resin used in the present invention is a polyacrylic acid and/or a salt thereof water absorbent resin having a constructional unit derived from acrylic acid, and an amount and a neutralization ratio thereof will be described later.

Out of constitutional units of a main chain exclusive of the cross-linking agent, generally 10 to 100 mol %, preferably to 100 mol %, more preferably 70 to 100 mol %, particularly preferably 90 to 100 mol % is a polymer derived from acrylic acid and/or a salt thereof. Further, it is preferable that substantially 100 mol % is a polymer derived from acrylic acid and/or a salt thereof.

Examples of the acrylic acid salt used in the present invention include acrylic acid monohydric salt such as: alkali metal salt such as lithium, sodium, and potassium; ammonium salt; and amine salt. It is preferable to use alkali metal salt. With respect to acid group, a neutralization ratio of the water absorbent resin obtained in the present invention preferably ranges from 10 to 99 mol %, more preferably from 20 to 99 mol %, still more preferably from 40 to 95 mol %, still further more preferably from 40 to 90 mol %, particularly preferably from 50 to 90 mol %, most preferably from 60 to 80 mol %. Note that, the neutralization may be carried out in a monomer phase before polymerization, or may be neutralized during and after polymerization, or these processes may be combined with each other. However, it is preferable that acrylic acid in a monomer phase is neutralized.

Note that, in the present invention, a water absorbent resin other than the polyacrylate and/or a salt thereof water absorbent resin may be used together, but an amount of the polyacrylate and/or a salt thereof water absorbent resin used as a main component preferably ranges from 50 to 100 wt %, more preferably from 70 to 100 wt %, most preferably from 90 to 100 wt %. In case of using that water absorbent resin together, examples thereof include polyamine water absorbent resin such as cross-linked polyethyleneimine and cross-linked polyalylamine; a nonionic water absorbent resin such as cross-linked polyacrylamide and cross-linked polyethyleneoxide; and the like.

(2) Particulate Water Absorbing Agent

The particulate water absorbing agent in the present invention refers to an aqueous liquid absorbing and solidifying agent including a water absorbent resin as a main component (the absorbing and solidifying agent is referred to also as "gelatinizer"). The aqueous liquid is not limited to water, but may be urine, blood, feces, waste fluid, moisture, vapor, ice, a mixture of water and organic solvent, a mixture of water and inorganic solvent, rain water, ground water, and the like, as long as the aqueous liquid includes water. It is preferable that the particulate water absorbing agent is an absorbing and solidifying agent which absorbs and solidifies urine, particularly human urine, out of the aforementioned aqueous liquids.

An amount of the water absorbent resin included in the particulate water absorbing agent of the present invention as a main component preferably ranges from 70 to 99.9 mass %, more preferably from 80 to 99.7 mass %, still more preferably from 90 to 99.5 mass %, with respect to the entire amount of the particulate water absorbing agent. Other than the water absorbent resin, water is preferably contained. It is more preferable that a specific amount (0.01 to 10 mass %, further, 0.1 to 5 mass %) of water is contained. Further, below-described additive may be used as required.

Note that, in the present invention, a shape of each particle is not specifically limited, and examples thereof include a spherical shape, a substantially spherical shape, an irregularly-pulverized shape, a bar shape, a polyhedral shape, an oblate shape (e.g., U.S. Pat. No. 4,973,632), a wrinkled shape (e.g., U.S. Pat. No. 5,744,564). The particles may be single particles or may be granulated particles or may be a mixture thereof. Further, each particle may be in a foamed porous manner. A favorable example of the particle is a single particle or a granulated particle which has an irregularly-pulverized shape.

(3) an Example of Production Method of Particulate Water Absorbing Agent

As to the particulate water absorbing agent of the present invention, an example of a production method thereof is a method for producing a particulate water absorbing agent containing a polyacrylic acid and/or a salt thereof as a main component, said method including the steps of: cross-linking and polymerizing a monomer aqueous solution containing acrylic acid and/or a salt thereof as a main component; and drying a hydrogel obtained by the polymerization, wherein α-hydroxycarboxylic acid and/or a salt thereof is added to the monomer aqueous solution at the time of polymerization or to the hydrogel cross-linked polymer after the polymerization (hereinafter, referred to also as "hydrogel"). Further, the method preferably includes any one of the following steps (A) to (G).

(A) A step of preparing a monomer component by mixing an unsaturated monomer containing acrylic acid and/or salt thereof as a main component with α-hydroxycarboxylic acid and/or a salt thereof and then polymerizing the prepared monomer component (step of adding and mixing α-hydroxycarboxylic acid before cross-linking and polymerizing a monomer aqueous solution containing an unsaturated monomer).

(B) A step of polymerizing the unsaturated monomer while adding and mixing α-hydroxycarboxylic acid, after adding a polymerization initiator and during the cross-linking and polymerizing treatment.

(C) A step of adding and mixing α-hydroxycarboxylic acid to the resultant hydrogel after cross-linking and polymerizing the monomer aqueous solution containing the unsaturated monomer.

(D) A step of, as necessary, obtaining dried powder in which an amount of particles having a particle diameter less than 150 μm is 0 to 5 mass % and a mass average particle diameter (D50) is 200 to 600 μm or less and a particle size distribution logarithmic standard deviation (σζ) is 0.20 to 0.40, after carrying out the steps (A) to (C).

(E) A step of carrying out surface cross-linking with respect to the powder obtained in the step (D).

(F) A step of further carrying out a surface treatment with polyhydric metal salt after carrying out the surface cross-linking in the step (E).

(G) A step of obtaining dried powder, in which 0 to 5 mass % of particles whose particle diameter is less than 150 μm is included and a mass average particle diameter (D50) ranges from 200 to 600 μm and a logarithmic standard deviation (σζ) of a particle size distribution ranges from 0.20 to 0.40, after any one of the steps (D) to (F) or after the step (F).

Hereinafter, the production method of the present invention will be further described.

(4) Unsaturated Monomer

In the present invention, acrylic acid and/or salt thereof is preferably used as the unsaturated monomer. The amount and neutralization ratio of acrylic acid and kinds of acrylic acid are as described in the item (1).

As to a method used in the present invention for producing acrylic acid, there were known, as industrial production methods, a vapor-phase contact oxidation method using propylene and/or acrolein, an ethylene cyanohydrin method, a high-pressure Reppe method, an improved Reppe method, a ketene method, an acrylonitrile hydrolysis method, and the like. Above all, it is most general to adopt the vapor-phase contact oxidation method using propylene and/or acrolein. Further, in the present invention, the acrylic acid obtained in accordance with the vapor-phase contact oxidation method is favorably used.

Further, in the present invention, an unsaturated monomer other than the acrylic acid and/or salt thereof may be used together within the foregoing range.

Generally, the acrylic acid obtained in accordance with the vapor-phase contact oxidation includes impurity, whose amount exceeds about 2000 ppm, other than the acrylic acid component. The impurity will be described later.

The acrylic acid used in the monomer of the present invention preferably contains a methoxyphenol. Examples of the methoxyphenol include: o, m, p-methoxyphenols; and a methoxyphenol further having a single or two or more substitutional groups such as methyl group, t-butyl group, and hydroxyl group. A preferable methoxyphenol is p-methoxyphenol. With respect to the acrylic acid, an amount of the methoxyphenol ranges from 10 to 200 mass ppm, preferably from 10 to 90 mass ppm, more preferably from 10 to 80 mass ppm, still more preferably from 10 to 70 mass ppm, particularly preferably from 10 to 50 mass ppm, most preferably from 10 to 30 mass ppm.

In case where the amount of p-methoxyphenol exceeds 200 mass ppm, the resultant water absorbent resin is colored (turns yellow). Further, in case where the amount of p-methoxyphenol is less than 10 mass ppm, particularly in case where the amount is less than 5 mass ppm, that is, in case where p-methoxyphenol serving as the polymerization inhibitor is removed by purification such as distillation, polymerization may be initiated before intentionally initiating the polymerization, and also a polymerization rate surprisingly becomes low.

Further, the acrylic acid of the present invention more preferably contains a smaller amount of protoanemonin and/or furfural as the impurity. The amount of protoanemonin and/or furfural is preferably 0 to 20 mass ppm. As the amount of protoanemonin and/or furfural increases, the resultant water absorbent resin is colored and a polymerization time (time taken to reach the polymerization peak temperature) and an amount of a residual monomer increase. Besides, an extractable polymer content more greatly increases than slight increase of the absorbency, so that the properties relatively decrease. In view of improvement of properties and characteristics of the water absorbent resin, the amount of protoanemonin and/or furfural contained in the acrylic acid preferably ranges from 0 to 10 mass ppm or less, more preferably from 0 to 5 mass ppm, still more preferably from 0.01 to 5 mass ppm, particularly preferably from 0.05 to 2 mass ppm, most preferably from 0.1 to 1 mass ppm.

Note that, examples of the monomer used together with the acrylic acid are monomers mentioned in below-described U.S. Patents and European Patents. Specific examples thereof include: water-soluble or hydrophobic unsaturated monomers such as methacrylic acid, malic acid (anhydride), fumaric acid, crotonic acid, itaconic acid, vinyl sulfonic acid, 2-(meth)acrylamide-2-methylpropane sulfonic acid, (meth)acryloxyalkane sulfonic acid and alkali metal salt thereof, ammonium salt, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethyleneglycol(meth)acrylate, polyethyleneglycol(meth)acrylate, isobutylene, lauryl(meth)acrylate, and the like.

(5) Internal Cross-Linking Agent

A cross-linking method adopted in the present invention is not particularly limited. Examples thereof include: a method in which a cross-linking agent is added during or after polymerization so as to carry out the cross-linking; a method in which a radical polymerization initiator is used to carry out radical cross-linking; a method in which an electron ray is used to carry out radiation cross-linking; and a similar method. It is preferable that a predetermined amount of internal cross-linking agent is added to the monomer beforehand and polymerization is carried out so as to carry out a cross-linking reaction at the same time as or after the polymerization.

Examples of the internal cross-linking agent used in the present invention include: polymerizable internal cross-linking agent such as N,N'-methylenebisacrylamide, (poly)ethyleneglycol di(meth)acrylate, (poly)propyleneglycol di(meth)acrylate, (polyoxiethylene)trimethylolpropanetri(meth)acrylate, trimethylolpropanedi(meth)acrylate, (poly)ethyleneglycol di($\beta$-acryloyloxipropionate), trimethylolpropane tri($\beta$-acryloyloxipropionate), and poly(meth)allyloxyalkane; and reactive internal cross-linking agent, which is reactive with carboxyl group, e.g., polyglycidyl ether (ethyleneglycol diglycidyl ether and the like), polyol (ethyleneglycol, polyethyleneglycol, glycerin, sorbitol, and the like). These internal cross-linking agents are used independently or two or more kinds of the internal cross-linking agent are used. Note that, in case of using one or more kinds of the internal cross-linking agent, it is preferable to essentially use the polymerizable internal cross-linking agent taking absorbent properties and the like of the resultant water absorbent resin into consideration.

In view of properties of the internal cross-linking agent, an amount of the internal cross-linking agent ranges from 0 to 3 mol %, preferably from 0.005 to 2 mol %, more preferably from 0.01 to 1 mol %, still more preferably from 0.05 to 0.2 mol %, with respect to the aforementioned monomer.

(6) $\alpha$-Hydroxycarboxylic Acid

The hydroxycarboxylic acid is carboxylic acid having a hydroxyl group in its molecule, and examples thereof include: aliphatic hydroxy acids such as lactic acid, glycolic acid, malic acid, glycerinic acid, tartaric acid, citric acid, isocitric acid, mevalonic acid, chinic acid, shikimic acid, $\beta$-hydroxypropionic acid, and salts thereof; and aromatic hydroxyl acids such as salicylic acid, creosote acid, vanillic acid, syringic acid, resocylic acid, pyrocatechuic acid, protocatechuic acid, genticic acid, orsellinic acid, mandelic acid, gallic acid, and salts thereof.

Above all, the hydroxycarboxylic acid used in the present invention refers to carboxylic acid whose $\alpha$-carbon in its molecule is coupled with a hydroxyl group, and preferably is aliphatic $\alpha$-hydroxycarboxylic acid such as non-polymer $\alpha$-hydroxycarboxylic acid, more preferably is aliphatic $\alpha$-hydroxycarboxylic acid having neither a cyclic structure nor an unsaturated group. It is not preferable to use aromatic $\alpha$-hydroxycarboxylic acid or cyclic or unsaturated $\alpha$-hydroxycarboxylic acid since aromatic $\alpha$-hydroxycarboxylic acid itself is colored due to oxidative reaction. Further, its molecular weight preferably ranges from 40 to 2000, more preferably from 60 to 1000, particularly preferably from 100 to 500. Further, it is preferable that the $\alpha$-hydroxycarboxylic acid used in the present invention is so water-soluble that its water solubility with respect to 100 g of deionized water at 20±5° C. is 1 g or more, more preferably 5 g or more, still more preferably 10 g or more, particularly preferably 20 g or more. Examples of such $\alpha$-hydroxycarboxylic acid include: lactic acid and/or a salt thereof, citric acid and/or a salt thereof, malic acid and/or a salt thereof, isocitric acid and/or a salt thereof, glyceric acid and/or a salt thereof, tartaric acid and/or a salt thereof; D-lactic acid and/or a salt thereof, D-citric acid and/or a salt thereof, D-malic acid and/or a salt thereof, D-isocitric acid and/or a salt thereof, D-glyceric acid and/or a salt thereof, D-tartaric acid and/or a salt thereof; L-lactic acid and/or a salt thereof, L-citric acid and/or a salt thereof, L-malic acid and/or a salt thereof, L-isocitric acid and/or a salt thereof, L-glyceric acid and/or a salt thereof, L-tartaric acid and/or a salt thereof; and meso-lactic acid and/or a salt thereof, meso-citric acid and/or a salt thereof, meso-malic acid and/or a salt thereof, meso-isocitric acid and/or a salt thereof, meso-glyceric acid and/or a salt thereof, meso-tartaric acid and/or a salt thereof.

The $\alpha$-hydroxycarboxylic acid particularly preferably used is lactic acid or $\alpha$-hydroxy polyhydric carboxylic acid which has, in its molecule, two or more carboxyl groups, preferably two to ten carboxyl groups, more preferably two to six carboxyl groups, still more preferably two to four carboxyl groups. In view of the absorbent properties and the improvement of coloring problem, it is most preferable to use malic acid and/or a salt thereof, citric acid and/or a salt thereof, isocitric acid and/or a salt thereof, and tartaric acid and/or a salt thereof, as the $\alpha$-hydroxy polyhydric carboxylic acid.

Further, in case where the $\alpha$-hydroxycarboxylic acid of the present invention is salt, it is preferable to use monohydric salt, e.g., alkali metal salt such as lithium, potassium, and sodium, or ammonium salt, or monohydric amine salt, in view of solubility with respect to water. Further, in case of using the $\alpha$-hydroxy polyhydric carboxylic acid as salt, the carboxylic acid may be entirely or partially salt.

When the $\alpha$-hydroxycarboxylic acid used in the present invention is $\alpha$-hydroxymonocarboxylic acid such as lactic acid and the like, in view of the absorbency properties and coloring prevention effect, an amount of the $\alpha$-hydroxymonocarboxylic acid generally ranges from 1 to 10 wt %, preferably from 1 to 5 wt %, particularly preferably from 1 to 4 wt %, most preferably from 1 to 3 wt %, with respect to the unsaturated monomer or the polymer thereof. Further, in case of using the $\alpha$-hydroxy polyvalent carboxylic acid favorably used in the present invention, in view of the absorbency properties and coloring prevention effect, an amount of the $\alpha$-hydroxy polyvalent carboxylic acid generally ranges from 0.01 to 10 wt %, preferably from 0.05 to 5 wt %, particularly preferably from 0.1 to 3 wt %, most preferably from 0.2 to 3 wt %, with respect to the unsaturated monomer or the polymer thereof.

(6) Preparation of Unsaturated Monomer Aqueous Solution

In case of carrying out reverse phase suspension polymerization or aqueous solution polymerization in the polymerization step, the unsaturated monomer is included in aqueous solution containing an internal cross-linking agent as required, and a concentration of the unsaturated monomer component in the aqueous solution (hereinafter, referred to as "monomer aqueous solution") preferably ranges from 10 to 70 mass %, more preferably from 15 to 65 mass %, still more preferably from 30 to 55 mass %, in view of properties. Note that, a solvent other than water may be used together as required, and a kind of the solvent used together is not particularly limited.

Particularly, as an example of a production method in which the α-hydroxycarboxylic acid and/or a salt thereof of the present invention is included in the water absorbent resin, how to mix the α-hydroxycarboxylic acid and/or a salt thereof to the monomer aqueous solution is not particularly limited. For example, α-hydroxycarboxylic acid and/or a salt thereof or α-hydroxycarboxylic acid and/or a salt thereof aqueous solution is mixed with a monomer or monomer aqueous solution, thereby preparing a monomer aqueous solution containing the α-hydroxycarboxylic acid and/or a salt thereof.

Further, in carrying out the polymerization, for example 0 to 50 wt %, preferably 0 to 20 wt % of water-soluble resin or water absorbent resin may be added to the monomer so as to improve properties of the water absorbent resin. Further, for example 0 to 5 mass %, preferably 0 to 1 mass % of various kinds of foaming agents (carbonate, azo compound, bubble, and the like), surfactant, chelating agent, and chain transfer agent such as hypophosphorous acid and/or a salt thereof and the like may be added so as to improve properties of the water absorbent resin.

Particularly, in view of polymerization reaction control, water absorbing performance and in view of coloring of power with time passage, it is preferable to use the α-hydroxycarboxylic acid and/or a salt thereof and the chelating agent in the present invention. Favorable examples of the chelating agent used together include: aminocarboxylic acid metallic chelating agents such as iminodiacetic acid, hydroxyethyl iminodiacetic acid, nitrilotriacetic acid, nitrilotripropionic acid, ethylenediamine tetraacetic, hydroxythylenediamine triacetic acid, hexamethylenediamine tetraacetic acid, diethyltriamine pentaacetic acid, triethylenetetraamine hexaacetic acid, trans-1,2-diaminocyclohexane tetraacetic acid, bis(2-hydroxyethyl)glycine, diaminopropanol tetraacetic acid, ethylenediamine-2-propionic acid, glycoletherdiamine tetraacetic acid, bis(2-hydroxybenzyl) ethylenediamine diacetic acid, 3-hydroxy-2,2-iminodisuccinate, iminodisuccinate, methylglycine diacetic acid and salts thereof; and aminophosphate metallic chelating agents such as ethylenediamine-N,N'-di(methylenephosphinic acid), ethylenediamine tetra(methylenephosphinic acid), nitriloacetic acid-di(methylenephosphinic acid), nitrilodiacetic acid-(methylenephosphinic acid), nitriloacetic acid-β-propionic acid-methylenephosphinic acid, nitrilotris(methylene phoshpinic acid), cyclohexanediamine tetra(methylenephosphonic acid), ethylene diamine-N,N'-diacetic acid-N,N'-di(methylenephosphonic acid), ethylenediamine-N,N'-di(methylenephosphonic acid), ethylenediamine tetra(methylenephosphonic acid), polymethylenediamine tetra(methylenephosphonic acid), diethylenetriamine penta(methylene phosphonic acid), 1-hydroxyethylidene diphosphonic acid, and salts thereof. Further, also a compound mentioned as an example in U.S. Pat. No. 659,989 can be used as the aminocarboxylic acid metallic chelating agent.

An amount of the chelating agent used together with the α-hydroxycarboxylic acid and/or a salt thereof ranges from 0.0001 to 1 mass %, preferably from 0.001 to 1 mass %, more preferably from 0.003 to 0.5 mass %, particularly preferably from 0.005 to 0.05 mass %, with respect to the monomer solid content.

Note that, in case of mixing the α-hydroxycarboxylic acid and/or a salt thereof with the monomer or the hydrogel, liquid, slurry, or solid (or powder) of the α-hydroxycarboxylic acid and/or a salt thereof may be mixed without any modification, or may be mixed by using solvent. The concentration and the solvent in mixing the α-hydroxycarboxylic acid and/or a salt thereof are not particularly limited, but generally 10 to 100 mass %, preferably 20 to 100 mass %, still more preferably 30 to 100 mass % of the aqueous solution is used.

(7) Polymerization Step

In polymerizing the unsaturated monomer aqueous solution, it is general that aqueous solution polymerization or reverse phase suspension polymerization is carried out in view of performance and easiness to control the polymerization. These polymerization methods can be carried out also in an air atmosphere, but it is preferable to carry out the polymerization in an inert gas atmosphere such as nitrogen and argon (for example, 1% or less of oxide). Further, it is preferable to use the monomer component for polymerization after its diffused oxide is sufficiently substituted by inert gas (for example, oxide is less than 1 ppm). The aqueous solution polymerization realizes high productivity and high properties, but it is conventionally difficult to control polymerization according to the aqueous solution polymerization. However, aqueous solution polymerization exemplified in the present invention is particularly favorable also in controlling the polymerization, and examples thereof in the present invention include continuous belt polymerization and continuous or batch kneader polymerization.

Note that, the reverse phase suspension polymerization is a polymerization method in which a monomer aqueous solution is suspended in a hydrophobic organic solvent, and is described for example in U.S. Patents such as U.S. Pat. No. 4,093,776, U.S. Pat. No. 4,367,323, U.S. Pat. No. 4,446,261, U.S. Pat. No. 4,683,274, U.S. Pat. No. 5,244,735, and the like. The aqueous solution polymerization is a method in which a monomer aqueous solution is polymerized without using any dispersion solvent. For example, the polymerization method is described in U.S. Pat. No. 4,625,001, U.S. Pat. No. 4,873, 299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,380,808, and the like, European Patent No. 0811636, European Patent No. 0955086, European Patent No. 0922717, European Patent No. 1178059, and the like. A monomer, a cross-linking agent, a polymerization initiator, and other additive that are described in these documents are applicable to the present invention.

According to the present invention, in polymerizing the monomer, it is more preferable that a total time period from preparation of the monomer component and/or neutralization of acrylic acid to initiation of polymerization is shorter for improvement of the absorbent properties and prevention of coloring (prevention of yellowing) which are objects of the present invention, and the total time period is preferably within 24 hours, more preferably within 12 hours, still more preferably within 3 hours, particularly preferably within an hour. From an industrial view, it is general that a residence time exceeds 24 hours due to mass neutralization and mass monomer component preparation in a tank, but it is less preferable that a time period from the monomer component preparation and/or acrylic acid neutralization is longer, which results in a larger amount of residual monomer and yellowing of the water absorbent resin. Therefore, in order to reduce the residence time, it is preferable to carry out batch polymerization or continuous polymerization through continuous neutralization and continuous monomer component preparation, and it is more preferable to carry out continuous polymerization.

In polymerizing the monomer aqueous solution, it is preferable to add a polymerization initiator such as: persulfate such as potassium persulfate, sodium persulfate, and ammonium persulfate; t-butylhydroperoxide, hydrogen peroxide, 2,2'-azobis(2-amidinopropane)dihydrochloride, 2-hydroxy-1-phenyl-propane-1-one, and benzoin methylether. Further, it is possible to use a redox initiator obtained by mixing with the foregoing polymerization initiator a reducer such as L-ascorbic acid for promoting decomposition of the polymerization initiator. An amount of the redox initiator generally ranges from 0.001 to 1 mol %, preferably from 0.001 to 0.5 mol %, with respect to the monomer.

Further, instead of the polymerization initiator, it is possible to use an activation energy ray such as a radiation ray, an electron ray, and an ultraviolet ray so as to carry out polymerization reaction. Further, irradiation of the activation energy ray and a polymerization initiator sensitized by a radiation ray, an electron ray, and an ultraviolet ray may be adopted together, or the irradiation of the activation energy ray and the aforementioned polymerization initiator may be adopted together.

Note that, a reaction temperature and a reaction time in the polymerization reaction are not particularly limited and are suitably determined depending on a type of the hydrophilic monomer or the polymerization initiator and a reaction temperature thereof. Generally, the polymerization reaction is carried out preferably at a temperature lower than the boiling point for three hours or less, more preferably an hour or less, still more preferably 0.5 hours or less. Further, a peak temperature thereof is preferably 150° C. or lower, more preferably 90 to 120° C. Further, it is preferable that water and acrylic acid evaporated at the time of polymerization are collected as required and the collected water and acrylic acid are recycled in the production steps of the water absorbent resin.

The method of the present invention for producing the particulate water absorbing agent is a method in which α-hydroxycarboxylic acid and/or a salt thereof is added to a monomer aqueous solution at the time of polymerization or a hydrogel cross-linked polymer after polymerization so as to produce the particulate water absorbing agent. A favorable example thereof is a method in which the α-hydroxycarboxylic acid and/or a salt thereof is added to the monomer aqueous solution at the time of polymerization. Note that, the monomer aqueous solution at the time of polymerization refers not only to the monomer aqueous solution before polymerization but also to a monomer aqueous solution during polymerization and a gelatinous substance including the aqueous solution. Further, the α-hydroxycarboxylic acid and/or a salt thereof is added to once or more times when a polymerization ratio of the monomer is 0 to 99 mol %, more preferably when the polymerization ratio is 0 to 70 mol %, particularly preferably when the polymerization ratio is 0 to 50 mol %.

An example of another production method is as follows. In case of adding the α-hydroxycarboxylic acid and/or a salt thereof to the monomer aqueous solution in the polymerization step, the α-hydroxycarboxylic acid and/or a salt thereof may be mixed at any timing before or after pouring the polymerization initiator, and the mixing timing and the mixing process are not particularly limited, but it is preferable that the α-hydroxycarboxylic acid and/or a salt thereof is added to the monomer aqueous solution before polymerization (polymerization ratio is 0%) or to the monomer aqueous solution whose polymerization ratio is less than 30%.

(8) Hydrogel Granulation (Fragmentation) Step

In case of the aqueous solution polymerization, the hydrogel cross-linked polymer (hereinafter, referred to as "hydrogel") obtained in the polymerization step may be dried without any modification, but the hydrogel is crushed by using a gel crusher as required and particles obtained by crushing the hydrogel is then dried. In view of properties, the hydrogel in being crushed is kept or heated at preferably 40 to 95° C., more preferably 50 to 80° C.

Further, in case of crushing the gel, it is possible to crush the gel by extruding the gel from a porous structure whose hole diameter is 0.3 to 20 mm. A shape of the hole is a cyclic shape, a tetragonal shape such as square and rectangular, a triangle shape, or a hexagonal shape, and is not particularly limited, but the shape is preferably a cyclic shape. Note that, the hole diameter can be defined by a diameter in case where an external periphery of a mesh is converted into an external periphery of a circle.

The hole diameter of the porous structure for extruding the hydrogel so as to obtain crushed gel particles is more preferably 0.5 to 10 mm, more preferably 0.5 to 5.0 mm.

If the hole diameter of the porous structure is less than 0.3 mm, the gel may be in a string manner or the gel may be unable to be extruded. Thus, it is not preferable to set the hole diameter to be less than 0.3 mm. If the hole diameter of the porous structure is more than 20 mm, it may be impossible to exhibit the effect of the present invention. Thus, it is not preferable to set the hole diameter to be more than 20 mm.

An example of a device for extruding the hydrogel so as to obtain crushed gel particles is a device arranged so that the hydrogel polymer is extruded from a porous plate so as to crush the hydrogel polymer. Further, examples of an extruding mechanism include: a screw type, a rotary type, and the like; and a type in which the hydrogel polymer is carried with pressure from its feed opening to its porous plate. The screw type extruder may be monoaxial or polyaxial. Generally, it is possible to use an extruder used to extrude and mold meat, rubber, and plastic, or it is possible to use an extruder used as a crusher. Examples thereof are a meat chopper and a dome gran.

As described above, the monomer aqueous solution which contains a specific amount of internal cross-linking agent and which has a specific concentration is polymerized, and the resultant hydrogel is extruded under a specific condition, i.e., the hydrogel is extruded from the porous structure whose hole diameter is 0.3 to 20 mm, thereby crushing the hydrogel. In this case, water, polyhydric alcohol exemplified as the internal cross-linking agent, a mixture solution of water and polyhydric alcohol, a solution obtained by dissolving polyhydric metal exemplified as the internal cross-linking agent or vapor thereof may be added to water.

The method of the present invention for producing the particulate water absorbing agent is a method in which α-hydroxycarboxylic acid and/or a salt thereof is added to a monomer aqueous solution at the time of polymerization or a hydrogel cross-linked polymer after polymerization so as to produce the particulate water absorbing agent. A preferable example of the production method is a method in which the α-hydroxycarboxylic acid and/or a salt thereof is mixed in granulating (fragmenting) the hydrogel.

Note that, a resin solid content (solid content) of the hydrogel in mixing the α-hydroxycarboxylic acid and/or a salt thereof is not particularly limited, but an amount of the resin solid content is preferably 10 to 70 mass %, more preferably 15 to 65 mass %, still more preferably 30 to 55 mass %. Note that, the solid content of the hydrogel will be described later.

(9) Drying Step

The fragmented hydrogel cross-linked polymer obtained in the aforementioned step, particularly, the hydrogel containing the α-hydroxycarboxylic acid and/or a salt thereof is dried under a specific temperature condition, and is crushed and classified as required, and the resultant is granulated and subjected to a surface cross-linking treatment under a specific temperature condition.

Further, in order to reduce the residual monomer and prevent yellowing as objects of the present invention, it is more preferable that also a time period from the polymerization to beginning of the drying step via the gel crushing step carried out as required is shorter. That is, the drying step carried out with respect to the hydrogel cross-linked polymer after the polymerization is started (the hydrogel cross-linked polymer is placed in a dryer) preferably within an hour, more preferably within 0.5 hours, still more preferably within 0.1 hour. Further, in order to reduce the residual monomer and allows the water absorbent resin to be less colored, a temperature of the hydrogel cross-linked polymer during a period from the polymerization to the drying step is preferably 50 to 80° C., more preferably 60 to 70° C.

From an industrial view point, it is general that the residence time after the polymerization exceeds three hours due to mass polymerization. However, if the time period from the polymerization to the beginning of the drying step is longer or the temperature deviates from the foregoing range, the amount of the residual monomer increases and the water absorbent resin is more colored. Thus, it is preferable to carry out continuous polymerization and continuous drying so as to reduce the residence time.

An amount of the resin solid content which is calculated from the drying loss (1 g of powder or particles is heated at 180° C. for three hours) is 80 mass % or more, more preferably from 85 to 99 mass %, still more preferably 90 to 98 mass %, particularly preferably 92 to 97 mass %. Further, the drying temperature is not particularly limited, but the drying temperature preferably ranges from 100 to 300° C., more preferably from 150 to 250° C. Various drying methods that can be adopted here are drying by heating, hot air drying, drying under reduced pressure, infrared drying, microwave drying, drying with a drum dryer, drying by azeotropy with a hydrophobic organic solvent, high humidity drying in which a high temperature steam is used, and the like drying methods. The hot air drying is carried out with a gas whose dew point is 40 to 100° C., more preferably 50 to 90° C. Note that, the drying and the polymerization may be carried out at the same time in the present invention.

(10) Particle Size and Adjustment Thereof after the Drying

After the aforementioned step of drying the hydrogel cross-linked polymer, the particle size may be adjusted as required after the drying, but it is preferable that the particle size is adjusted to a specific value in order to improve properties in below-described surface cross-linking. The particle size can be suitably adjusted by polymerization (particularly, reverse phase suspension polymerization), crushing, classification, granulation, fine powder collection, and the like.

A mass average particle diameter (D50) before the surface cross-linking ranges from 200 to 600 µm, preferably from 200 to 550 µm, more preferably from 250 to 500 µm, still more preferably from 300 to 450 µm, particularly preferably from 350 to 400 µm. Further, it is more preferable that the resultant contains a smaller amount of particles whose particle diameter is less than 150 µm. The amount of particles whose particle diameter is less than 150 µm generally ranges from 0 to 5 mass %, more preferably from 0 to 3 mass %, particularly preferably from 0 to 1 mass %. Further, it is more preferable that the resultant contains a smaller amount of particles whose particle diameter is 850 µm or more, and the amount of the particles whose particle diameter is 850 µm or more generally ranges from 0 to 5 mass %, preferably from 0 to 3 mass %, particularly preferably from 0 to 1 mass %. A logarithmic standard deviation ($\sigma\zeta$) of particle size distribution preferably ranges from 0.20 to 0.40, more preferably from 0.27 to 0.37, still more preferably from 0.25 to 0.35.

(11) Surface Cross-Linking Step

The surface cross-linking of the water absorbent resin refers to a condition under which a portion whose cross-linking density is higher is provided on a surface layer (vicinity of a surface: generally, several dozens µm from the surface) of the water absorbent resin having an even cross-linked structure in the polymer, and a highly cross-linked layer may be formed through surface radical cross-linking or surface polymerization, and the surface cross-linking may be carried out by cross-linking reaction with a surface cross-linking agent. The following will further describe the surface cross-linking carried out with the surface cross-linking agent as required in the present invention.

It is possible to use various organic or inorganic cross-linking agents as the surface cross-linking agent used in the present invention. However, in view of properties, there are used a cross-linking agent which is reactable with a carboxyl group, particularly, an organic surface cross-linking agent, generally, a polyhydric alcohol compound, an epoxy compound, a polyhydric amine compound or its condensate with a haloepoxy compound, an oxazoline compound, a mono, di, or polyoxazolidinone compound, a polyhydric metal salt, an alkylenecarbonate compound, and the like.

Specific examples of the surface cross-linking agent used in the present invention are described in U.S. Pat. No. 6,228,930, U.S. Pat. No. 6,071,976, U.S. Pat. No. 6,254,990, and the like. The specific examples include: polyhydric alcohol compound such as mono, di, tri, tetra, polyethyleneglycol, monopropyleneglycol, 1,3-propanediol, dipropyleneglycol, 2,3,4-trimethyl-1,3-pentandiol, polypropyleneglycol, glycerin, polyglycerin, 2-butene-1,4-diol, 1,4-butandiol, 1,3-butandiol, 1,5-pentandiol, 1,6-hexanediol, and 1,2-cyclohexanedimethanol; epoxy compounds such as ethyleneglycol diglycidyl ether and glycidol; polyhydric amine compounds such as ethylenediamine, diethylenetriamine, triethylenetetramine, tetraethylenepentamine, pentaethylenehexamine, and polyethyleneimine, and polyamidepolyamine; haloepoxy compounds such as epichlorohydrin, epibromhydrin, and α-methyl epichlorohydrin; a condensate of the polyhydric amine compound and the haloepoxy compound; oxazolidinone compounds such as 2-oxazolidinone; alkylene carbonate compounds such as ethylenecarbonate, but the surface cross-linking agent is not particularly limited. In order to maximize the effect of the present invention, it is preferable to use the polyhydric alcohol out of these cross-linking agents. The polyhydric alcohol has 2 to 10 carbon atoms in its molecule, preferably 3 to 8 carbon atoms in its molecule.

An amount of the surface cross-linking agent is determined depending on a compound to be used or a combination of compounds. However, with respect to 100 parts by mass of resin solid content, the amount of the surface cross-linking agent preferably ranges from 0.001 parts by mass to 10 parts by mass, more preferably from 0.01 parts by mass to 5 parts by mass. In the present invention, it is preferable to use water in the surface cross-linking. In this case, an amount of water to be used is determined depending on a moisture content of the water absorbent resin to be used, but the amount of water generally ranges from 0.5 to 20 parts by mass, more preferably from 0.5 to 10 parts by mass with respect to 100 parts by mass of the water absorbent resin. Further, in the present invention, not only water but also a hydrophilic organic solvent may be used. In this case, an amount of the hydrophilic organic solvent to be used generally ranges from 0 to 10 parts by mass, more preferably from 0 to 3 parts by mass, with respect to 100 parts by mass of the water absorbent resin. In view of the mixing property and stability, a temperature of the cross-linking solution preferably ranges from 0° C. to the boiling point, more preferably from 5 to 50° C., still more preferably from 10 to 30° C. Further, in view of the mixing property, a temperature of the water absorbent resin before the mixture preferably ranges from 0 to 80° C., more preferably from 40 to 70° C.

Further, in the present invention, out of various mixing methods, it is preferable to adopt a method in which water and/or hydrophilic organic solvent is mixed beforehand and then an aqueous solution thereof is sprayed or dropped onto the water absorbent resin. It is more preferable to spray the aqueous solution to the water absorbent resin. An average diameter of the sprayed droplet preferably ranges from 1 to 300 µm, more preferably from 10 to 200 µm. At the time of mixture, water-insoluble fine powder or surfactant may coexist as long as this coexistence does not impair the effect of the present invention, for example, with its amount ranging from 0 to 10 mass % or less, preferably from 0 to 5 mass %, more preferably from 0 to 1 mass %. The surfactant used and an amount thereof are mentioned in International Application No. WO2005JP1689 (filing date of the international application: Feb. 4, 2005).

A favorable mixer used in the aforementioned mixture is required to generate a great mixing power for even mixture. Various mixers are used as the mixer usable in the present invention, but it is preferable to use a high-speed stirring mixer, particularly, it is preferable to use a high-speed stirring continuous mixer. Examples thereof include Turbulizer (commercial name: product of Hosokawa Micron in Japan) and Lödige mixer (commercial name: product of Lödige in Germany) and the like.

The water absorbent resin after the mixture of the surface cross-linking agent is preferably subjected to a heating treatment. The heating treatment is carried out under the following conditions: A heating temperature preferably ranges from 120 to 250° C., more preferably from 150 to 250° C., and a heating time preferably ranges from one minute to two hours. The heating treatment can be carried out by using a general dryer or heating oven. Examples of the dryer include a trenched mixing dryer, rotary dryer, disk dryer, fluidized bed dryer, air dryer, and infrared dryer. Further, the heated water absorbent resin may be cooled down as required.

Note that, these surface cross-linking methods are described in European Patent No. 0349240, European Patent No. 0605150, European Patent No. 0450923, European Patent No. 0812873, European Patent No. 0450924, European Patent No. 066808, and the like, Japanese Publication for Unexamined Patent Application, Tokukaihei 7-242709, Japanese Publication for Unexamined Patent Application, Tokukaihei 7-224304, and the like, U.S. Pat. No. 5,409,771, U.S. Pat. No. 5,597,873, U.S. Pat. No. 5,385,983, U.S. Pat. No. 5,610,220, U.S. Pat. No. 5,633,316, U.S. Pat. No. 5,674,633, U.S. Pat. No. 5,462,972, and the like, International Publication No. WO099/42494, International Publication No. WO099/43720, International Publication No. WO099/42496, and the like, and also these surface cross-linking methods are applicable to the present invention.

(12) Polyhydric Metal Salt Surface Treatment

In the particulate water absorbing agent of the present invention, it is possible to achieve the desired absorbent properties by carrying out a surface treatment with polyhydric metal salt (referred to also as "inorganic surface cross-linking agent) as required, particularly by using the polyhydric metal salt together with the organic surface cross-linking agent for surface cross-linking. Note that, in carrying out the surface cross-linking by using the organic surface cross-linking agent and the polyhydric metal salt together, the surface cross-linking is carried out with the polyhydric metal salt before, at the same time as, or after the organic surface cross-linking. In mixing the polyhydric metal salt, it is preferable to mix the aforementioned α-hydroxycarboxylic acid and/or a salt thereof with water-soluble polyhydric metal salt.

Examples of the polyhydric metal salt used include water-soluble polyhydric metal salts such as aluminum chloride, polyaluminum chloride, aluminum sulfate, aluminum nitrate, his aluminum potassium sulfate, his aluminum sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, and zirconium nitrate. Also in view of solubility with respect to absorbed liquid such as urine, it is preferable to use salt having crystal water thereof.

As the polyhydric metal salt used, it is particularly preferable to use an aluminum compound. Above all, it is preferable to use aluminum chloride, poly aluminum chloride, aluminum sulfate, aluminum nitrate, his aluminum potassium sulfate, his aluminum sodium sulfate, potassium alum, ammonium alum, sodium alum, sodium aluminate. Aluminum sulfate is particularly preferable. It is possible to most favorably use powder of hydrated crystal such as aluminum sulfate octadecahydrate and aluminum sulfate hydrate (tetradecahydrate to octadecahydrate). These components may be independently used or in a suitable combination of two or more kinds. An amount thereof is within the range of the aforementioned organic surface cross-linking agent.

Note that, a method, a condition, and the like of the polyhydric metal salt surface treatment are described in International Publication No. 2004/69915, International Publication No. 2004/113452, and International Publication No. 2005/108472, and these polyhydric metal salt surface treatment methods are adopted.

(13) Particulate Water Absorbing Agent (First Particulate Water Absorbing Agent)

As exemplified in the production method, the present invention gives a novel particulate water absorbing agent. That is, the present invention provides a novel particulate water absorbing agent including a polyacrylic acid and/or a salt thereof water absorbent resin as a main component, wherein the water absorbent resin internally includes α-hydroxycarboxylic acid and/or a salt thereof.

According to the present invention, the water absorbent resin internally includes α-hydroxycarboxylic acid and/or a salt thereof or α-hydroxy polyhydric carboxylic acid and/or a salt thereof, so that it is possible to realize, for example, high and well balanced properties such as an absorbency against pressure (AAP), a centrifuge retention capacity (CRC), a saline flow conductivity (flow conductivity with respect to 0.69 mass % of sodium chloride aqueous solution: SFC) which are required, and it is possible to effectively prevent coloring.

According to the present invention, α-hydroxycarboxylic acid and/or a salt thereof contained and evenly distributed in the water absorbent resin is coupled with a substance which causes the water absorbent resin to be colored, thereby preventing the water absorbent resin from being colored. In case where the α-hydroxycarboxylic acid and/or a salt thereof locally exists on the surface side of the water absorbent resin, a surface free from any α-hydroxylic acid is exposed at the surface of the water absorbent resin when the water absorbent resin is swollen or when moisture is absorbed, so that the coloring of the water absorbent resin may be less prevented. Thus, a larger amount of the α-hydroxycarboxylic acid and/or a salt thereof is used, which may result in lower properties (centrifuge retention capacity or absorbency, liquid permeability, and the like) of the water absorbent resin.

For example, in case of adding α-hydroxycarboxylic acid and/or a salt thereof to the water absorbent resin as in techniques disclosed by Japanese Unexamined Patent Publication Tokukai 2000-327926, Japanese Unexamined Patent Publication Tokukai 2003-52742, and Japanese Unexamined Patent Publication Tokukai 2005-186016, oxycarboxylic acid (hydroxycarboxylic acid) exists in the vicinity of the surface of the water absorbent resin, so that this influences reactivity of the surface cross-linking agent or the polyhydric metal salt. Thus, this causes the desired absorbent property, particularly, the saline flow conductivity (SFC) to decrease. Further, according to techniques disclosed by Japanese Unexamined Patent Publication Tokukai 2003-206305, Japanese Unexamined Patent Publication Tokukai 2003-206381, International Publication No. 2005/012369 Pamphlet, it is substantially impossible to prevent the coloring, and the resultant absorbent properties are low. In contrast, the particulate water absorbing agent which can be obtained by the present invention and whose water absorbent resin internally includes the α-hydroxycarboxylic acid and/or a salt thereof has such advantage that water absorbent properties opposite to each other can be improved, particularly, improvement of the saline flow conductivity and the coloring prevention effect can be realized at the same time.

Further, an amount of the α-hydroxycarboxylic acid and/or a salt thereof contained in the water absorbent resin ranges from 0.1 to 10 mass %, preferably from 0.1 to 5 mass %, more preferably from 0.15 to 3 mass %, most preferably from 0.2 to 3 mass %, with respect to the particulate water absorbing agent. If the amount of the α-hydroxycarboxylic acid and/or a salt thereof contained in the water absorbent resin deviates from the foregoing range, it is difficult to realize both the absorbent property (particularly, SFC) and the coloring prevention effect.

Note that, the fact that the α-hydroxycarboxylic acid and/or a salt thereof exists not only on the surface but also inside the water absorbent resin can be clarified as follows: for example, the water absorbent resin is crushed by a crusher such as a high-speed homogenizer, and then the crushed resultant is classified by a JIS metal gauze, so as to carry out extraction for each particle size by using a hydrophilic organic solvent or the like, thereby carrying out quantitative analysis or the like with respect to the amount of the α-hydroxycarboxylic acid and/or a salt thereof.

(14) Particulate Water Absorbing Agent (Second Particulate Water Absorbing Agent)

As an example of the foregoing production method, the present invention gives a novel particulate water absorbing agent. That is, the present invention is to provide a novel particulate water absorbing agent containing a polyacrylic acid and/or a salt thereof water absorbent resin as a main component, wherein the water absorbent resin internally includes α-hydroxycarboxylic acid and/or a salt thereof, and the water absorbing agent satisfies at least one of the following conditions (a) to (c).

(a) An amount of particles having a particle diameter less than 150 μm is 0 to 5 mass % and a mass average particle diameter (D50) is 200 to 600 μm and a logarithmic standard deviation (σζ) of particle size distribution is 0.20 to 0.40.

(b) An absorbency against pressure (AAP) indicative of an absorbency with respect to 0.90 mass % sodium chloride aqueous solution against a pressure of 4.8 kPa for 60 minutes is at least 15 g/g.

(c) A flow conductivity with respect to 0.69 mass % of sodium chloride aqueous solution (SFC) is at least $5 \times (10^{-7} \cdot cm^3 \cdot s \cdot g^{-1})$.

The novel particulate water absorbing agent satisfying at least one of the foregoing conditions essentially includes α-hydroxycarboxylic acid and/or a salt thereof and, preferably, satisfies the conditions (a) and (b), the conditions (a) and (c), or the conditions (b) and (c), particularly preferably, satisfies all the conditions (a) to (c).

The following describes properties (a) to (c), more preferable properties (d) to (g) of the first or second particulate water absorbing agent of the present invention which can be obtained as an example of the foregoing production method.

(a) Particle Size

As to the particulate water absorbing agent of the present invention, it is preferable to control the particle size thereof to the following specific particle sizes. These particle sizes are suitably adjusted by pulverization, classification, fine powder collection, and the like.

That is, a mass average particle diameter (D50) of the particulate water absorbing agent is 200 to 600 μm, preferably 350 to 600 μm, more preferably 360 to 500 μm, particularly preferably 360 to 450 μm. As the mass average particle diameter is smaller, the whiteness of the water absorbent resin is greater and the coloring is less apparent, but the smaller mass average particle diameter is not preferable since the water absorbent property, particularly, the liquid permeability under pressure remarkably decreases. Further, in case where the mass average particle diameter is equal to or less than the foregoing range, the anti-urine property (gel deterioration preventing effect) is impaired, so that this may be a problem in practical use for a diaper or the like. Further, it is more preferable that an amount of fine powder whose particle diameter is less than 150 μm is smaller. The amount of the fine power is adjusted to generally 0 to 10 mass %, more preferably 0 to 3 mass %, particularly preferably 0 to 1 mass %. Further, it is more preferable that an amount of particles whose particle diameter is 850 μm or more is smaller. The amount of the particles is adjusted to generally 0 to 5 mass %, preferably 0 to 3 mass %, particularly preferably 0 to 1 mass %. The logarithmic standard deviation (σζ) of particle size distribution is preferably 0.20 to 0.40, more preferably 0.27 to 0.37, further more preferably 0.25 to 0.35.

In case where the logarithmic standard deviation deviates from the foregoing particle size distribution, the particulate water absorbing agent exhibits less effect in being used as an absorbing article such as a disposable diaper or the like.

Further, a bulk density (defined by JIS K-3362) of the particulate water absorbing agent is preferably 0.40 to 0.90 g/ml, more preferably 0.50 to 0.80 g/ml. Further, an amount of particles whose particle diameter ranges from 600 to 150 μm preferably ranges from 60 to 100 mass %, more preferably from 70 to 100 mass %, still more preferably from 80 to 100 mass %, with respect to the entire amount.

(b) Absorbency Against Pressure (AAP) where the Pressure is 4.8 kPa

As an example of means for achieving the surface cross-linking of the particulate water absorbing agent of the present invention, the particulate water absorbing agent has an absorbency against pressure (AAP) of preferably 15 (g/g) or more, more preferably 18 (g/g) or more, still more preferably 20

(g/g) or more, particularly preferably 22 (g/g) or more, most preferably 25 (g/g) or more, with respect to 0.9 mass % of sodium chloride aqueous solution against a pressure of 4.8 kPa.

In case where the absorbency against pressure of 4.8 kPa (AAP) is less than 18 (g/g), when the water absorbing agent is used in a diaper for example, a so-called re-wet is large which results in skin rash of a baby. Thus, it is not preferable that the absorbency against pressure is less than 18 (g/g). It is more preferable that the AAP is greater, and an upper limit of the AAP is not particularly limited. However, in view of balance with other properties, the upper limit is preferably 50 (g/g) or less, more preferably 45 (g/g) or less, still more preferably 40 (g/g) or less.

(c) Saline Flow Conductivity (Flow Conductivity with Respect to 0.69 Mass % of Sodium Chloride Aqueous Solution: SFC)

As an example of means for achieving the surface cross-linking of the particulate water absorbing agent of the present invention, the particulate water absorbing agent has a saline flow conductivity (flow conductivity with respect to 0.69 mass % of sodium chloride aqueous solution: SFC) of preferably $5(\times 10^{-7}\,cm^3 \cdot s \cdot g^{-1})$ or more, more preferably $10(\times 10^{-7}\,cm^3 \cdot s \cdot g^{-1})$ or more, still more preferably $30(\times 10^{-7}\,cm^3 \cdot s \cdot g^{-1})$ or more, still further more preferably $50(\times 10^{-7}\,cm^3 \cdot s \cdot g^{-1})$ or more, particularly preferably $70(\times 10^{-7}\,cm^3 \cdot s \cdot g^{-1})$ or more, most preferably $100(\times 10^{-7}\,cm^3 \cdot s \cdot g^{-1})$ or more.

In case where the saline flow conductivity (SFC) is less than $5(\times 10^{-7}\,cm^3 \cdot s \cdot g^{-1})$, when concentration of the particulate water absorbing agent in a core of a diaper is 30 mass % or more, more specifically, when concentration of the particulate water absorbing agent in a core of a diaper is 50 mass % or more, a rate at which urine is absorbed is low. This may result in leakage.

(d) Centrifuge Retention Capacity (CRC)

As an example of means for achieving the surface cross-linking of the particulate water absorbing agent of the present invention, the particulate water absorbing agent has a centrifuge retention capacity (CRC) of preferably 10 (g/g) or more, more preferably 20 (g/g) or more, still more preferably 25 (g/g) or more, particularly preferably 30 (g/g) or more, with respect to 0.9 mass % sodium chloride aqueous solution. It is more preferable that an upper limit of the centrifuge retention capacity (CRC) is higher, and the centrifuge retention capacity (CRC) is not particularly limited. However, in view of balance with other properties, the centrifuge retention capacity (CRC) is preferably 50 (g/g) or less, more preferably 45 (g/g) or less, still more preferably 40 (g/g) or less.

When the centrifuge retention capacity (CRC) is less than 10 (g/g), an amount of absorbed liquid is so small that the particulate water absorbing agent is not suitable for use in a sanitary material such as a diaper. Further, when the centrifuge retention capacity (CRC) exceeds 50 (g/g), its gel strength is low, so that it may be impossible to obtain a water absorbing agent which is superior in liquid permeability.

(e) Amount of Water Soluble Component (Extractable Polymer Content)

As an example of means for achieving the surface cross-linking of the particulate water absorbing agent of the present invention, the particulate water absorbing agent has an extractable polymer content of preferably 0 to 35 mass %, more preferably 25 mass % or less, still more preferably 15 mass % or less, particularly preferably 10 mass % or less. In case where the extractable polymer content exceeds 35 mass %, its gel strength may be low and its liquid permeability may be low. Further, in case where the particulate water absorbing agent is used in a diaper for an extended period of time, absorption capacities (CRC and AAP) may drop as time elapses.

(f) Coloring-with-Time Stability

The particulate water absorbing agent obtained in the present invention can be favorably used in a sanitary material such as a disposable diaper. At the time of usage in the sanitary material, the particulate water absorbing agent keeps its greatly clean whiteness also under a long-time storage condition with high humidity and temperature. Further, as to the water absorbent resin obtained in accordance with the foregoing production method, its particles exposed for seven days in an atmosphere whose temperature is 70±1° C. and relative humidity is 65±1% are subjected to Hunter's Lab color system measurement by using a spectral colorimeter. In this color system measurement, the water absorbing agent shows such coloring-with-time stability that its L value (Lightness) is at least 70, more preferably 74 or more, particularly preferably 78 or more. (Note that, an upper limit of the L value is generally 100. However, even when the upper limit is 70, this does not raise any problem in practical use.)

Further, its yellow index (YI value: see European Patent No. 942014 and European Patent No. 1108745) preferably ranges from 0 to 15, more preferably from 0 to 13, still more preferably from 0 to 10, most preferably from 0 to 5. It is preferable that the particulate water absorbing agent is hardly yellowed. Further, a change rate of the yellow index after coloring promotion test carried out for 14 days at a temperature of 70° C.±1 and a relative humidity of 95±1% defined in Examples is 100 to 150%, preferably 100 to 140%, more preferably 200 to 130%, most preferably 100 to 120%. In this manner, even when the particulate water absorbing agent is exposed to harsh temperature and humidity, the particulate water absorbing agent greatly prevents yellowing.

(h) Residual Monomer

As an example of means for achieving the surface cross-linking of the particulate water absorbing agent of the present invention, the particulate water absorbing agent has a residual monomer whose amount ranges from 0 to 400 mass ppm, more preferably from 0 to 300 mass ppm, still more preferably from 0 to 200 mass ppm, particularly preferably from 0 to 100 mass ppm.

(20) Other Additives

In order to provide various functions as a required function, the particulate water absorbing agent may include not only the α-hydroxycarboxylic acid and/or a salt thereof and a chelating agent but also: an oxidizer, and a reducing agent such as a sulfite (hydrogen) salt; water-insoluble inorganic or organic powder such as silica and metal soap; deodorant agents; antibacterial agents; polymer polyamines; pulps; thermoplastic fibers; and the like so that 0 to 3 mass %, preferably, 0 to 1 mass % of the aforementioned additive is added to the water absorbent resin. Note that, the aforementioned additives are detailed in Japanese Unexamined Patent Publication Tokugan 2005-109779, and the descriptions thereof are applicable to the present invention.

Above all, it is preferable that the chelating agent mentioned in U.S. Pat. No. 6,599,989 and U.S. Pat. No. 6,469,080 is included so that an amount thereof preferably ranges from 0.001 to 3 wt %, more preferably from 0.01 to 2 wt %.

(21) Purpose of Use

The purpose of use of the particulate water absorbing agent of the present invention is not particularly limited. However, it is preferable to use the particulate water absorbing agent for absorbing articles such as a disposable diaper, a sanitary napkin, and an incontinence pad. Particularly, the particulate water absorbing agent is favorably used for a high concentration diaper (a diaper containing a large amount of water absorbent resin) which conventionally raised problems such as odor derived from a material of the particulate water absorbing agent, coloring, and the like. Particularly, in case where the particulate water absorbing agent is used for an absorbent core top layer of the absorbing article, it is possible to exhibit particularly excellent properties.

The absorbing article of the present invention includes: (a) the particulate water absorbing agent, (b) an absorbent core obtained by forming a hydrophilic fiber into a sheet shape as required, (c) a liquid permeable front sheet, and (d) a liquid impermeable back sheet. The absorbent core in case where the hydrophilic fiber is not used is arranged by fixing the water absorbing agent onto paper and/or nonwoven fabric. Further, in case where the particulate water absorbing agent is blended or sandwiched with a fiber material (pulp), the fiber material used is, for example, crushed wood pulp, a cotton linter, or a hydrophilic fiber such as a cross-linked cellulose fiber, rayon, cotton, wool, acetate, or vinylon. These fiber materials are preferably aerated.

The absorbent core contains the particulate water absorbing agent at an amount (core concentration) of 30 to 100 mass %, preferably 40 to 100 mass %, more preferably 50 to 100 mass %, still more preferably 60 to 100 mass %, particularly preferably 70 to 100 mass %, most preferably 75 to 95 mass %, thereby exhibiting the effect of the present invention. For example, in case of using the particulate water absorbing agent with the aforementioned concentration, particularly in case of using the particulate water absorbing agent for an absorbent core top layer, high liquid permeability (liquid permeability potential under pressure) results in an excellent diffusion property with respect to absorbed liquid such as urine, so that it is possible to provide an absorbing article such as a disposable diaper whose absorption amount is increased due to efficient liquid distribution and whose absorbent core keeps its sanitary whiteness.

Further, it is preferable that the absorbent core is compression molded to a density of 0.06 g/cc or more and 0.50 g/cc or less and a basic weight of 0.01 g/cm$^2$ or more and 0.20 g/cm$^2$ or less.

EXAMPLES

Through the following Examples, the present invention is further described. However, the present invention is not limited to the following Examples and the like, as long as the present invention is interpreted in light of a gist thereof. Further, properties (a) to (g) recited in claims or described in the Examples were measured in the following measurement methods. Note that, the following measurement methods are described as measurement carried out with respect to the particulate water absorbing agent, but the measurement is identical to measurement carried out with respect to the water absorbent resin in terms of values thereof.

Note that, in case where an electric device used in Examples is not particularly specified, a voltage adopted therein was entirely 200V or 100V. Further, in case where a water absorbent resin is not particularly specified, the water absorbent resin was used at 25±2° C. and with a relative humidity of 50±5% RH. As reagents and tools exemplified in the following measurement method and Examples, alternative reagents and tools may be suitably used. Further, unless particularly mentioned, mass and weight are synonymous, and "mass %" and "wt %" are the same meaning. Further, "ppm" refers to "mass ppm (wt ppm)", and "part" refers to "part by mass (part by weight)".

(a) Particle Size

On the basis of WO2004/069404, the water absorbent resin (or the particulate water absorbing agent) was sieved by using JIS standard sieves (JIS Z8801-1 (2000)) respectively having mesh sizes of 850 μm, 710 μm, 600 μm, 500 μm, 425 μm, 300 μm, 212 μm, 150 μm, 106 μm, 45 μm, and the like, and a residual percentage R was plotted on a logarithmic probability paper. Then, a particle diameter was read as the mass average particle diameter (D50). Further, the logarithmic standard deviation (σζ) is represented by the following equation. As a value of σζ is smaller, the particle diameter distribution is narrower.

$$\sigma\zeta = 0.5 \times \ln(X2/X1)$$

where X1 is a particle diameter in case where R=84.1% and X2 is a particle diameter in case where R=15.9%.

(b) Absorbency Against Pressure (AAP)

On the basis of U.S. Pat. No. 6,228,930, U.S. Pat. No. 6,071,976, and U.S. Pat. No. 6,254,990, an absorbency against pressure (load) for a physiological saline was measured. In accordance with the method described in each of the aforementioned U.S. Patents, a predetermined load (4.8 kPa) was exerted onto 0.9 g of the particulate water absorbing agent and a mass of 0.9 mass % sodium chloride aqueous solution absorbed by the particulate water absorbing agent with time passage was calculated from a measurement value obtained by using a scale. Separately, the same operation was carried out without using the particulate water absorbing agent, and a mass of physiological saline absorbed by a filter paper or the like other than the particulate water absorbing agent was calculated from a measurement value obtained by using a scale, and the calculation result was regarded as a blank value. Subsequently, correction was made by subtracting the blank value, and the mass of the physiological saline actually absorbed by the particulate water absorbing agent was divided by the mass (0.9 g) of the particulate water absorbing agent, thereby calculating the absorbency against pressure (g/g) with a load of 4.8 kPa.

(c) Flow Conductivity with Respect to 0.69 Mass % of Sodium Chloride Aqueous Solution (SFC)

A flow conductivity with respect to 0.69 mass % of sodium chloride aqueous solution (SFC) is a value indicative of liquid permeability in case where the water absorbent resin particles or the particulate water absorbing agent is swollen. As the value of SFC is higher, the liquid permeability is higher.

A test was carried out on the basis of an SFC test described in U.S. Pat. No. 5,849,405.

By using a device shown in FIG. 1, the water absorbent resin particles or the particulate water absorbing agent (0.9 g) evenly spread in a container 40 was swollen in a synthesized urine (1) under a pressure of 0.3 psi (2.07 kPa) for 60 minutes, and a height of a gel layer of a gel 44 was recorded. Then, under a pressure of 0.3 psi (2.07 kPa), 0.69 mass % sodium chloride aqueous solution 33 was made to flow from a tank 31 and to pass through the swollen gel layer at a constant hydrostatic pressure. The SFC test was carried out at a room temperature (20 to 25° C.). By using a computer and a scale, an amount of liquid passing through the gel layer at intervals of 20 seconds was recorded for 10 minutes as a time function. A flow rate Fs(t) of the solution passing through the swollen gel 44 (mainly between particles thereof) was determined in terms of g/s by dividing an increasing weight (g) by an increasing time (s). A time in which a constant hydrostatic pressure and a stable flow rate had been obtained was set as "ts", and only data obtained between "ts" and a ten-minute interval was used to calculate the flow rate, the flow rate calculated between "ts" and a ten-minute interval was used to calculate a value of Fs (t=0), i.e., a first flow rate of the solution passing through the gel layer. Fs (t=0) was calculated by extrapolating, into t=0, a result obtained by carrying out least square of Fs (t) and a duration.

Flow Conductivity with Respect to 0.69 Mass % of Sodium Chloride Aqueous Solution (SFC)

$$= (Fs(t = 0) \times L0)/(\rho \times A \times \Delta P)$$
$$= (Fs(t = 0) \times L0)/139506$$

Here,

Fs (t=0): a flow rate represented by "g/s"

L0: a height of the gel layer that is represented by "cm"

$\rho$: a density (1.003 g/cm$^3$) of NaCl solution

A: an area (28.27 cm$^2$) on the upper side of the gel layer of the cell 41

$\Delta P$: a hydrostatic pressure (4920 dyne/cm$^2$) exerted to the gel layer. Further, a unit of the saline flow conductivity (SFC) is ($10^{-7} \cdot cm^3 \cdot s \cdot g^{-1}$).

In the device shown in FIG. 1, a glass tube 32 was inserted into the tank 31, and a lower end of the glass tube 32 was disposed so that 0.69 mass % sodium chloride aqueous solution 33 was positioned 5 cm higher than a bottom of the swelling gel 44 in the cell 41. 0.69 mass % sodium chloride aqueous solution 33 contained in the tank 31 was supplied to the cell 41 via an L-shaped tube 34 with a cock. A collecting container 48 for collecting liquid having passed through the gel layer was disposed under the cell 41, and the collecting container 48 was placed on an even balance 49. An inside diameter of the cell 41 was 6 cm, and No. 400 stainless metal gauze (38 μm in mesh) 42 was placed on a bottom of a lower portion of the cell 41. A hole 47 which allowed liquid to pass through was provided on a lower portion of a piston 46, and a glass filter 45 having high permeability was provided on the bottom thereof so that the particulate water absorbing agent or the swelling gel did not enter into the hole 47. The cell 41 was placed on a table for the cell, and the table's surface which is in contact with the cell was positioned on the stainless metal gauze 43 which did not prevent the liquid from passing through.

The synthesized urine (1) was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of ammonium dihydrogen phosphate, and 994.25 g of pure water.

(d) Centrifuge Retention Capacity (GVs/CRC)

0.2 g of particulate water absorbing agent was evenly contained in a bag (60 mm×60 mm) made of a nonwoven fabric and was sealed. Then, the bag was soaked in 100 g of 0.9 mass % sodium chloride aqueous solution (physiological saline) whose temperature was 25(±3)° C., and was withdrawn 60 minutes later. By using a centrifugal separator, the bag was drained for three minutes at 250G, and a weight W1 (g) of the bag was measured. Further, the same operation was performed without using the particulate water absorbing agent, and a weight W2 (g) was measured. Then, from the weights W1 and W2, the absorbency in this case was calculated according to the following Expression 1.

$$GVs = [(W1-W2)/0.2-1] \quad \text{Expression 1}$$

(e) Amount of Water-Soluble Polymer (Referred to Also as "Amount of an Extractable Content" or "Extractable Content")

184.3 g of a 0.90 mass % sodium chloride aqueous solution was measured and poured into a 250 ml plastic container having a cover. Into the solution, 1.00 g of the particulate water absorbing agent was added, and the solution was stirred for 16 hours, thereby extracting an extractable content from the resin. The extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured so as to be used as a measurement solution.

First, only the physiological saline was titrated by using a 0.1N NaOH solution, until pH of the physiological saline reached 10. Thereafter, the physiological saline was titrated by using a 0.1N HCl solution, until pH of the physiological saline reached 2.7. In this way, blank titration amounts ([bNaOH]ml and [bHCl]ml) were measured. The same operation was performed with respect to the measurement solution, thereby measuring titration amounts ([NaOH]ml and [HCl]ml). Thereafter, for example, in case of a particulate water absorbing agent including a known amount of acrylic acid and its sodium salt, an amount of an extractable content (whose main component is the extracted water-soluble polymer) in the particulate water absorbing agent was calculated, in accordance with the following Expression 2, from an average molecular mass of the monomer and the titration amounts obtained by the foregoing operation. In case of a particulate water absorbing agent including an unknown amount of acrylic acid and its sodium salt, an average molecular mass of the monomer was calculated by using a neutralization ratio calculated by titration. The neutralization ratio was calculated in accordance with the following Expression 3.

$$\text{Amount of extractable content(wt \%)} = 0.1 \times (\text{average molecular mass}) \times 184.3 \times 100 \times ([HCl]-[bHCl])/1000/1.0/50.0 \quad \text{Expression 2}$$

$$\text{Neutralization ratio(mol \%)} = (1-([NaOH]-[bNaOH])/([HCl]-[bHCl])) \times 100 \quad \text{Expression 3}$$

(f) Coloring Evaluation with Respect to Particulate Water Absorbing Agent (Yellow Index/YI Value)

The coloring of the particulate water absorbing agent was evaluated by using a spectral colorimeter SZ-Σ80 COLOR MEASURING SYSTEM (product of NIPPON DENSHOKU). About 6 g of the water absorbent resin or the particulate water absorbing agent (corresponding to about 60% of a built-in sample table) was placed in the built-in sample container under a preset condition (reflection measurement/accessory powder-paste sample container (internal diameter of 30 mm and height of 12 mm/powder-paste standard rounded white plate No. 2/30Φ floodlight pipe serving as a standard)). Then, a surface color (YI value (Yellow Index)) was measured by the spectral colorimeter at room temperature (20 to 25° C.) and humidity of 50 RH %. Further, other object colors (L, a, b) or WB (Hunter color) can be measured at the same time by using the same device and the same measuring method. As a value indicative of L/WB is higher and a value indicative of a/b is lower, the water absorbent resin or the particulate water absorbing agent is less colored and its color is closer to substantial whiteness.

Subsequently, about 6 g of the particulate water absorbing agent was placed in the paste sample container, and the paste sample container containing the particulate water absorbing agent was exposed for 14 days in a constant-temperature-and-moisture apparatus (PLATINOUS LUCIFFER PL-2G, product of TABAI ESPEC CORPORATION) in which temperature had been adjusted to 70±1° C. and relative humidity had been adjusted to 90±1%. After the exposure, a surface color (YI value/Yellow Index)) was measured by the spectral colorimeter.

Note that, an yellow index change rate is represented by an YI change rate (%) after leaving the particulate water absorbing agent for 14 days at temperature of 70±1° C. and relative humidity of 90±1%, and the YI change rate (%) was calculated in accordance with the following Expression 8.

Yellow Index change rate(%)=(yellow index after exposure)/(yellow index before exposure)×100      Expression 8

(g) Residual Monomer

As to a residual monomer (residual acrylic acid and/or a salt thereof) of the particulate water absorbing agent, a two-hour-stirred filtrate having been additionally prepared in the foregoing item (e) was subjected to UV analysis by liquid chromatography, thereby analyzing a residual monomer amount ppm (with respect to the particulate water absorbing agent). Further, as to an amount of the residual monomer of the hydrogen which had not been dried, the fragmented hydrogel including about 0.5 g of a resin solid content was stirred for 16 hours, and a filtrate thereof was subjected to UV analysis by liquid chromatography in the same manner, and solid content correction was carried out, thereby calculating the amount of the residual monomer of the hydrogel.

(h) Coloring Evaluation with Respect to Particulate Water Absorbing Agent (Hunter's Lab Color System/L Value)

The coloring of the particulate water absorbing agent was evaluated by using a spectral colorimeter SZ-Σ80 COLOR MEASURING SYSTEM (product of NIPPON DENSHOKU). As a measurement condition, reflection measurement was adopted, and an accessory powder-paste sample container having an internal diameter of 30 mm and a height of 12 mm, a powder-paste standard rounded white plate No. 2, and a 30Φ floodlight pipe serving as a standard were used. About 5 g of the particulate water absorbing agent was placed in a built-in sample container. This corresponded to about 60% of the built-in sample container. Then, a surface L value (Lightness) was measured by the spectral colorimeter at room temperature (20 to 25° C.) and humidity of 50 RH %. The measured value was regarded as "lightness before exposure". As the measured value is higher, the color of the particulate water absorbing agent is closer to substantial whiteness.

Further, other object colors a, b (chromaticity) or YI (yellow index) or WB (white balance) can be measured at the same time by using the same device and the same measuring method. As a value indicative of WB is higher and a value indicative of YI/a/b is lower, the particulate water absorbing agent is less colored and its color is closer to substantial whiteness.

Subsequently, about 5 g of the particulate water absorbing agent was placed in the powder-paste sample container, and the paste sample container containing the particulate water absorbing agent was exposed for 7 days in a constant-temperature-and-moisture apparatus (PLATINOUS LUCIFFER PL-2G, product of TABAI ESPEC CORPORATION) in which temperature had been adjusted to 70±1° C. and relative humidity had been adjusted to 65±1%. This exposure was carried out as a 7-day coloring promotion test. After the exposure, a surface L value (Lightness) was measured by the spectral colorimeter. The measured value was regarded as "L value (Lightness) in a Hunter's Lab color system of particles having been exposed 7 days at temperature of 70±1° C. and relative humidity of 65±1%".

Production Example 1

A commercial acrylic acid (superfine reagent produced by Wako Pure Chemical Industries, Ltd.: containing 200 ppm of p-methoxyphenol) obtained by gas phase contact oxidization was supplied to a bottom of a high boiling impurity separation cylinder including 50 porous plates having no dam, and the acrylic acid was distilled at a reflux ratio of 1, and the resultant was further distilled again, thereby obtaining acrylic acid (0) made of 99% or more of acrylic acid and a minute amount of impurity (mainly water). In the acrylic acid (0), an amount of p-methoxyphenol was ND (less than 1 mass ppm) and each of amounts of protoanemonin, furfural, β-hydroxypropionic acid, and acrylic acid dimer was ND (less than 1 mass ppm). Further, in the acrylic acid (0), an amount of phenothiazine was 0 ppm, each of amounts of aldehyde and maleic acid was 1 ppm or less, and each of amounts of acetic acid and propionic acid was 20 ppm.

Subsequently, 50 ppm of p-methoxyphenol was added to the acrylic acid (0), thereby obtaining an acrylic acid (1).

As a polymerization tool, there was prepared a 10 L stainless double-arm kneader internally coated with Teflon (registered trademark) and equipped with a jacket. The kneader was also equipped with two sigma vanes whose rotational diameter was 120 mm and a lid for sealing the system. 376.3 g of acrylic acid (1) having been obtained in Production Example 1, 3983 g of sodium acrylate aqueous solution (2) serving as a neutralizer, 640.7 g of ion exchange water, 0.10 mol % (with respect to an entire unsaturated monomer) of polyethyleneglycol diacrylate (average additional mol number n=8.2) serving as an internal cross-linking agent, and 0.2 mol % (with respect to the entire unsaturated monomer) of D,L-malic acid were mixed with 50 mass % of malic acid aqueous solution, thereby obtaining a monomer aqueous solution.

Further, a temperature of the monomer aqueous solution was kept at 22° C. and was poured into a sigma type double-arm kneader, and nitrogen gas was injected therein so as to replace the system with nitrogen so that dissolved oxygen was 1 ppm or less. Next, warm water was led into the jacket, and sodium persulfate (0.09 g/mol) and L-ascorbic acid (0.005 g/mol) were added to the aqueous solution as polymerization initiator while stirring the monomer aqueous solution, thereby initiating polymerization. The polymerization was initiated when a predetermined time period had passed, and the polymerization was promoted while fragmenting the generated polymer gel, and further polymerization was carried out for 20 minutes after temperature thereof became a peak, thereby obtaining a hydrogel cross-linked polymer (1) fragmented into pieces each of which had a diameter of 1 to 2 mm.

Production Example 2

The same operation as in Production Example 1 was carried out except that D,L-malic acid was not used, thereby obtaining a hydrogel cross-linked polymer (2). The resultant hydrogel cross-linked polymer (2) and 0.2 mol % (with respect to the entire unsaturated monomer) of D,L-malic acid were mixed with 50 mass % malic acid aqueous solution for an hour by using the sigma type double-arm kneader, thereby obtaining a hydrogel cross-linked polymer (3).

Example 1

The hydrogel polymer (1) was spread out on a metal gauze whose mesh size was 850 μm, and was dried by hot air at 180° C. and at dew point of 70° C. for 90 minutes. A dry polymer thus obtained was crushed by using a vibrating mill, and then classified by using a JIS 850 μm standard sieve. Thus, dry powder particles (1) having passed through the sieve was obtained (average particle diameter was 300 μm, σζ was 0.35, particles whose particle diameter was less than 150 μm was 2%). Subsequently, in 100 parts by mass of thus obtained dry powder particles (1), a surface cross-linking solvent including 0.4 parts by mass of 1,4-butanediol, 0.6 parts by mass of propyleneglycol, 3.0 parts by mass of ion exchange water, and 0.5 parts by mass of isopropanol ("parts by mass" is indicative of a mass ratio with respect to the particles having passed through the sieve), was sprayed and mixed. Further, the mixture was then thermally processed at 210° C. for 40 minutes, thereby obtaining surface cross-linked particles (1). 2.02 parts by mass of aluminum sulfate treatment solution was added to 100 parts by mass of the surface cross-linked particles (1), and the resultant was dried by hot air at 60° C. for an hour so as to carry out polyhydric metal salt surface treatment, thereby obtaining a particulate water absorbing agent (1).

The aluminum sulfate treatment solution used was obtained by mixing 0.2 parts by mass of 50% sodium lactate aqueous solution (Musashino Chemical Laboratory, Ltd.) and 0.2 parts by mass of propyleneglycol with 2 parts by mass of tap water liquid aluminum sulfate 27 mass % solution (Asada Chemical Industry Co., Ltd.).

Example 2

The same operation as in Example 1 was carried out except that the hydrogel cross-linked polymer (3) obtained in Production Example 2 was used, thereby obtaining a particulate water absorbing agent (2).

Comparative Example 1

The same operation as in Example 1 was carried out except that the hydrogel cross-linked polymer (2) obtained in Production Example 2 was used, thereby obtaining a comparative particulate water absorbing agent (1).

Comparative Example 2

On the basis of Example 1 described in International Publication No. 2005/012369 pamphlet, a comparative particulate water absorbing agent (2) was obtained.

Properties of the particulate water absorbing agents (1) and (2) and the comparative particulate water absorbing agents (1) and (2) are shown in Table 1.

Example 3

In a 1-liter propylene container surrounded by foam polystyrene serving as a heat insulator and having an internal diameter of 80 mm, there were prepared: a solution (A) obtained by mixing 184.01 g of acrylic acid, 1.27 g of polyethyleneglycol diacrylate (molecular weight was 523), 2.25 g of 1.0 mass % diethylenetriamine penta acetic acid/trisodium salts aqueous solution, and 5.60 g of 10 mass % malic acid aqueous solution; and a solution (B) obtained by mixing 153.74 g of 48.5 mass % sodium hydrate aqueous solution and 142.92 g of ion exchange water whose temperature was adjusted to 50° C. The solution (B) was quickly added to and mixed with the solution (A) having been stirred by a magnetic stirrer, thereby obtaining a monomer aqueous solution (C). A temperature of the monomer aqueous solution (C) rose to about 100° C. due to neutralization heat and dissolution heat.

Next, 10.2 g of 3 wt % sodium persulfate aqueous solution was added to the monomer aqueous solution (C) while being stirred, and the mixture was quickly poured into an open system of a stainless tray-type container whose surface had been heated to 100° C. by a hot plate (commercial name: NEO HOTPLATE H1-1000, produced by Iuchi Seieidou) and whose bottom of 250×250 mm was internally coated with Teflon (registered trademark). The stainless tray-type container had the bottom of 250×250 mm, a top of 640×640 mm, and a height of 50 mm, and its central cross section had a trapezoidal shape, and its top was open.

Right after the monomer aqueous solution had been poured into the tray, polymerization was initiated. The monomer aqueous solution generated moisture vapor and its polymerization was promoted while its foam was vertically and horizontally expanding. Thereafter, the resultant shrank into a size slightly larger than the bottom. The expansion and shrinkage finished within about one minute. After the resultant was kept in the polymerization container for 4 minutes, a hydropolymer (hydrogel) was retrieved. Note that, a series of these operations was carried out in an open system.

The resultant hydropolymer (hydrogel) was crushed by a meat chopper, thereby obtaining a hydropolymer (crushed hydrogel particles) fragmented into pieces each of which had a diameter of several millimeters.

The fragmented crushed gel particles were spread out on a metal gauge of 20 mesh (mesh size was 850 μm) and were dried by hot air at 180° C. for 30 minutes, and the dried particles were pulverized by a roll mill and classified by JIS standard sieves having mesh size of 850 μm and mesh size of 150 μm respectively, thereby obtaining a particulate water absorbing agent (3) (solid content was 96 mass %). Properties of the particulate water absorbing agent (3) are shown in Tables 2 and 3.

Example 4

In a 1-liter propylene container surrounded by foam polystyrene serving as a heat insulator and having an internal diameter of 80 mm, there were prepared: a solution (A) obtained by mixing 184.01 g of acrylic acid, 1.27 g of polyethyleneglycol diacrylate (molecular weight was 523), 2.25 g of 1.0 mass % diethylenetriamine penta acetic acid/trisodium salts aqueous solution, and 11.19 g of 10 mass % malic acid aqueous solution; and a solution (B) obtained by mixing 153.74 g of 48.5 mass % sodium hydrate aqueous solution and 137.33 g of ion exchange water whose temperature was adjusted to 50° C. The solution (B) was quickly added to and mixed with the solution (A) having been stirred by a magnetic stirrer, thereby obtaining a monomer aqueous solution (C). A temperature of the monomer aqueous solution (C) rose to about 100° C. due to neutralization heat and dissolution heat.

Next, 10.2 g of 3 wt % sodium persulfate aqueous solution was added to the monomer aqueous solution (C) while being stirred, and the mixture was quickly poured into an open system of a stainless tray-type container whose surface had been heated to 100° C. by a hot plate (commercial name: NEO HOTPLATE H1-1000, produced by Iuchi Seieidou) and whose bottom of 250×250 mm was internally coated with Teflon (registered trademark). The stainless tray-type container had the bottom of 250×250 mm, a top of 640×640 mm, and a height of 50 mm, and its central cross section had a trapezoidal shape, and its top was open.

Right after the monomer aqueous solution had been poured into the tray, polymerization was initiated. The monomer aqueous solution generated moisture vapor and its polymerization was promoted while its foam was vertically and horizontally expanding. Thereafter, the resultant shrank into a size slightly larger than the bottom. The expansion and shrinkage finished within about one minute. After the resultant was kept in the polymerization container for 4 minutes, a hydropolymer (hydrogel) was retrieved. Note that, a series of these operations was carried out in an open system.

The resultant hydropolymer (hydrogel) was crushed by a meat chopper, thereby obtaining a hydropolymer (crushed hydrogel particles) fragmented into pieces each of which had a diameter of several millimeters.

The fragmented crushed gel particles were spread out on a metal gauge of 20 mesh (mesh size was 850 μm) and were dried by hot air at 180° C. for 30 minutes, and the dried particles were pulverized by a roll mill and classified by JIS standard sieves having mesh size of 850 μm and mesh size of 150 μm respectively, thereby obtaining a particulate water absorbing agent (4) (solid content was 96 mass %). Properties of the particulate water absorbing agent (4) are shown in Tables 2 and 3.

Comparative Example 3

In a 1-liter propylene container surrounded by foam polystyrene serving as a heat insulator and having an internal diameter of 80 mm, there were prepared: a solution (A) obtained by mixing 184.01 g of acrylic acid and 1.27 g of polyethyleneglycol diacrylate (molecular weight was 523); and a solution (B) obtained by mixing 153.74 g of 48.5 mass % sodium hydrate aqueous solution and 150.77 g of ion exchange water whose temperature was adjusted to 50° C. The solution (B) was quickly added to and mixed with the solution (A) having been stirred by a magnetic stirrer, thereby obtaining a monomer aqueous solution (C). A temperature of the monomer aqueous solution (C) rose to about 100° C. due to neutralization heat and dissolution heat.

Next, 10.2 g of 3 wt % sodium persulfate aqueous solution was added to the monomer aqueous solution (C) while being stirred, and the mixture was quickly poured into an open system of a stainless tray-type container whose surface had been heated to 100° C. by a hot plate (commercial name: NEO HOTPLATE H1-1000, produced by Iuchi Seieidou) and whose bottom of 250×250 mm was internally coated with Teflon (registered trademark). The stainless tray-type container had the bottom of 250×250 mm, a top of 640×640 mm, and a height of 50 mm, and its central cross section had a trapezoidal shape, and its top was open.

Right after the monomer aqueous solution had been poured into the tray, polymerization was initiated. The monomer aqueous solution generated moisture vapor and its polymerization was promoted while its foam was vertically and horizontally expanding. Thereafter, the resultant shrank into a size slightly larger than the bottom. The expansion and shrinkage finished within about one minute. After the resultant was kept in the polymerization container for 4 minutes, a hydropolymer (hydrogel) was retrieved. Note that, a series of these operations was carried out in an open system.

The resultant hydropolymer (hydrogel) was crushed by a meat chopper, thereby obtaining a hydropolymer (crushed hydrogel particles) fragmented into pieces each of which had a diameter of several millimeters.

The fragmented crushed gel particles were spread out on a metal gauge of 20 mesh (mesh size was 850 μm) and were dried by hot air at 180° C. for 30 minutes, and the dried particles were pulverized by a roll mill and classified by JIS standard sieves having mesh size of 850 μm and mesh size of 150 μm respectively, thereby obtaining a comparative particulate water absorbing agent (3) (solid content was 96 mass %). Properties of the comparative particulate water absorbing agent (3) are shown in Tables 2 and 3.

Example 5

In a reaction container formed by providing a lid on a 10-liter stainless double-arm kneader equipped with two sigma vanes and a jacket, 11.40 g of polyethyleneglycol diacrylate was dissolved in 5402 g of sodium acrylate aqueous solution whose neutralization ratio was 75 mol % so as to prepare a reaction solution (monomer concentration: 38 mass %). The polyethyleneglycol diacrylate serving as an internal cross-linking agent was such that an average additional mol number n of ethyleneoxide was 8.2. Further, the reaction solution was poured into a sigma-type double-arm kneader while keeping a temperature of the reaction solution at 25° C., and nitrogen gas was injected into the kneader so as to carry out replacement with nitrogen so that oxide dissolved in the system was 1 mass ppm or less. Subsequently, 28.1 g of 10 wt % sodium persulfate and 23.42 g of 0.1 wt % L-ascorbic acid aqueous solution were added to the reaction solution while stirring the reaction solution in the reaction container. About 20 seconds later, a temperature of the monomer aqueous solution became 25.5° C. and its polymerization was initiated. In two minutes after the initiation of the polymerization, a solution (A) obtained by mixing 20.74 g of 1.0 mass % diethylenetriamine penta acetic acid/trisodium salts aqueous solution (diethylenetriamine penta acetic acid/trisodium salts corresponds to 100 mass ppm with respect to the monomer) and 10.37 g of 10 mass % malic acid aqueous solution (malic acid corresponds to 0.25 mass % with respect to the monomer) was added to the polymer solution. Note that, polymerization of the polymer solution was promoted at the time when the solution (A) was added, but there were a lot of liquid substances.

The polymerization was carried out while crushing the gel generated by the polymerization. In 14 minutes after initiating the polymerization, temperature thereof became a polymerization peak temperature of 96° C. Further, in 34 minutes after initiating the polymerization, a hydrogel cross-linked polymer was retrieved.

The resultant hydrogel cross-linked polymer was fragmented into pieces each of which had a diameter of about 5 mm. The fragmented hydrogel cross-linked polymer particles were spread out on a metal gauze of 20 mesh (mesh size was 850 μm), and was dried by hot air at 180° C. for 45 minutes. Subsequently, a dry polymer thus obtained was crushed by using a roll mill, and then classified by using a JIS standard sieves whose mesh sizes were 850 μm and 150 μm respectively and then were blended, thereby obtaining such a particulate water absorbing agent (5) that a weight average particle diameter was 305 μm, σζ was 0.35, particles whose particle diameter was less than 150 μm was 2% with respect to entire particles. Properties of the particulate water absorbing agent (5) are shown in Tables 2 and 3.

Example 6

In a reaction container formed by providing a lid on a 10-liter stainless double-arm kneader equipped with two sigma vanes and a jacket, 11.40 g of polyethyleneglycol diacrylate was dissolved in 5395.6 g of sodium acrylate aqueous solution whose neutralization ratio was 75 mol % so as to prepare a reaction solution (monomer concentration: 38 mass %). The polyethyleneglycol diacrylate serving as an internal cross-linking agent was such that an average additional mol number n of ethyleneoxide was 8.2. Further, the reaction solution was poured into a sigma-type double-arm kneader while keeping a temperature of the reaction solution at 25° C., and nitrogen gas was injected into the kneader so as to carry out replacement with nitrogen so that oxide dissolved in the system was 1 mass ppm or less. Subsequently, 28.1 g of 10 wt % sodium persulfate and 23.42 g of 0.1 wt % L-ascorbic acid aqueous solution were added to the reaction solution while stirring the reaction solution in the reaction container. About 20 seconds later, a temperature of the monomer aqueous solution became 25.5° C. and its polymerization was initiated. In one minute after the initiation of the polymerization, a solution (B) obtained by mixing 20.74 g of 1.0 mass % diethylenetriamine penta acetic acid/trisodium salts aqueous solution (diethylenetriamine penta acetic acid/trisodium salts corresponds to 100 mass ppm with respect to the monomer) and 20.74 g of 10 mass % malic acid aqueous solution (malic acid corresponds to 0.5 mass % with respect to the monomer) was added to the polymer solution. Note that, polymerization of the polymer solution was promoted at the time when the solution (B) was added, but there were a lot of liquid substances.

The polymerization was carried out while crushing the gel generated by the polymerization. In 14 minutes after initiating the polymerization, temperature thereof became a polymerization peak temperature of 96° C. Further, in 34 minutes after initiating the polymerization, a hydrogel cross-linked polymer was retrieved.

The resultant hydrogel cross-linked polymer was fragmented into pieces each of which had a diameter of about 5 mm. The fragmented hydrogel cross-linked polymer particles were spread out on a metal gauze of 20 mesh (mesh size was 850 μm), and was dried by hot air at 180° C. for 45 minutes. Subsequently, a dry polymer thus obtained was crushed by using a roll mill, and then classified by using a JIS standard sieves whose mesh sizes were 850 μm and 150 μm respectively and then were blended, thereby obtaining such a particulate water absorbing agent (6) that a weight average particle diameter was 305 μm, σζ was 0.35, particles whose particle diameter was less than 150 μm was 2% with respect to entire particles. Properties of the particulate water absorbing agent (6) are shown in Tables 2 and 3.

Example 7

In a reaction container formed by providing a lid on a 10-liter stainless double-arm kneader equipped with two sigma vanes and a jacket, 11.40 g of polyethyleneglycoldiacrylate was dissolved in 5406.0 g of sodium acrylate aqueous solution whose neutralization ratio was 75 mol % so as to prepare a reaction solution (monomer concentration: 38 mass %). The polyethyleneglycol diacrylate serving as an internal cross-linking agent was such that an average additional mol number n of ethyleneoxide was 8.2. Further, the reaction solution was poured into a sigma-type double-arm kneader while keeping a temperature of the reaction solution at 25° C., and nitrogen gas was injected into the kneader so as to carry out replacement with nitrogen so that oxide dissolved in the system was 1 mass ppm or less. Subsequently, 28.1 g of 10 wt % sodium persulfate and 23.42 g of 0.1 wt % L-ascorbic acid aqueous solution were added to the reaction solution while stirring the reaction solution in the reaction container. About 20 seconds later, a temperature of the monomer aqueous solution became 25.5° C. and its polymerization was initiated. In two minutes after the initiation of the polymerization, a solution (B) obtained by mixing 20.74 g of 1.0 mass % 3-hydroxy-2,2'-iminoditetrasodium succinate aqueous solution (3-hydroxy-2,2'-iminoditetrasodium succinate corresponds to 100 mass ppm with respect to the monomer) and 10.37 g of 50 mass % malic acid aqueous solution (malic acid corresponds to 0.25 mass % with respect to the monomer) was added to the polymer solution. Note that, polymerization of the polymer solution was promoted at the time when the solution (B) was added, but there were a lot of liquid substances.

The polymerization was carried out while crushing the gel generated by the polymerization. In 14 minutes after initiating the polymerization, temperature thereof became a polymerization peak temperature of 95° C. Further, in 34 minutes after initiating the polymerization, a hydrogel cross-linked polymer was retrieved.

The resultant hydrogel cross-linked polymer was fragmented into pieces each of which had a diameter of about 5 mm. The fragmented hydrogel cross-linked polymer particles were spread out on a metal gauze of 20 mesh (mesh size was 850 μm), and was dried by hot air at 180° C. for 45 minutes. Subsequently, a dry polymer thus obtained was crushed by using a roll mill, and then classified by using a JIS standard sieves whose mesh sizes were 850 μm and 150 μm respectively and then were blended, thereby obtaining such a particulate water absorbing agent (7) that a weight average particle diameter was 300 μm, σζ was 0.35, particles whose particle diameter was less than 150 μm was 2% with respect to entire particles. Properties of the particulate water absorbing agent (7) are shown in Tables 2 and 3.

Example 8

In a reaction container formed by providing a lid on a 10-liter stainless double-arm kneader equipped with two sigma vanes and a jacket, 11.40 g of polyethyleneglycol diacrylate was dissolved in 5406.0 g of sodium acrylate aqueous solution whose neutralization ratio was 75 mol % so as to prepare a reaction solution (monomer concentration: 38 mass %). The polyethyleneglycol diacrylate serving as an internal cross-linking agent was such that an average additional mol number n of ethyleneoxide was 8.2. Further, the reaction solution was poured into a sigma-type double-arm kneader while keeping a temperature of the reaction solution at 25° C., and nitrogen gas was injected into the kneader so as to carry out replacement with nitrogen so that oxide dissolved in the system was 1 mass ppm or less. Subsequently, 28.1 g of 10 wt % sodium persulfate and 23.42 g of 0.1 wt % L-ascorbic acid aqueous solution were added to the reaction solution while stirring the reaction solution in the reaction container. About 20 seconds later, a temperature of the monomer aqueous solution became 25.5° C. and its polymerization was initiated. In two minutes after the initiation of the polymerization, a solution (B) obtained by mixing 20.74 g of 5.0 mass % (S,S)-ethylenediamine trisodium succinate aqueous solution ((S,S)-ethylenediamine trisodium succinate corresponds to 100 mass ppm with respect to the monomer) and 10.37 g of 50 mass % malic acid aqueous solution (malic acid corresponds to 0.25 mass % with respect to the monomer) was added to the polymer solution. Note that, polymerization of the polymer solution was promoted at the time when the solution (B) was added, but there were a lot of liquid substances.

The polymerization was carried out while crushing the gel generated by the polymerization. In 14 minutes after initiating the polymerization, temperature thereof became a polymerization peak temperature of 96° C. Further, in 34 minutes after initiating the polymerization, a hydrogel cross-linked polymer was retrieved.

The resultant hydrogel cross-linked polymer was fragmented into pieces each of which had a diameter of about 5 mm. The fragmented hydrogel cross-linked polymer particles were spread out on a metal gauze of 20 mesh (mesh size was 850 μm), and was dried by hot air at 180° C. for 45 minutes. Subsequently, a dry polymer thus obtained was crushed by using a roll mill, and then classified by using a JIS standard sieves whose mesh sizes were 850 μm and 150 μm respectively and then were blended, thereby obtaining such a particulate water absorbing agent (8) that a weight average particle diameter was 305 μm, σζ was 0.35, particles whose particle diameter was less than 150 μm was 2% with respect to entire particles. Properties of the particulate water absorbing agent (8) are shown in Tables 2 and 3.

Example 9

In 100 parts by mass of the particulate water absorbing agent (5) obtained in Example 5, a surface cross-linking agent including 0.4 parts by mass of 1,4-butanediol, 0.6 parts by mass of propyleneglycol, and 3.0 parts by mass of ion exchange water was sprayed and mixed. Further, the mixture was then thermally processed at 210° C. for 40 minutes, thereby obtaining surface cross-linked particles (2). 2.02 parts by mass of aluminum sulfate treatment solution was added to 100 parts by mass of the surface cross-linked particles (2), and the resultant was dried by hot air at 60° C. for an hour so as to carry out polyhydric metal salt surface treatment, thereby obtaining a particulate water absorbing agent (9).

The aluminum sulfate treatment solution used was obtained by mixing 0.2 parts by mass of 50% sodium lactate aqueous solution (Musashino Chemical Laboratory, Ltd.) and 0.2 parts by mass of propyleneglycol with 2 parts by mass of tap water liquid aluminum sulfate 27 mass % solution (Asada Chemical Industry, Co., Ltd.). Properties of the particulate water absorbing agent (9) are shown in Tables 2 and 3.

Example 101

In 100 parts by mass of the particulate water absorbing agent (6) obtained in Example 6, a surface cross-linking agent including 0.4 parts by mass of 1,4-butanediol, 0.6 parts by mass of propyleneglycol, and 3.0 parts by mass of ion exchange water was sprayed and mixed. Further, the mixture was then thermally processed at 210° C. for 40 minutes, thereby obtaining surface cross-linked particles (3). 2.02 parts by mass of aluminum sulfate treatment solution was added to 100 parts by mass of the surface cross-linked particles (3), and the resultant was dried by hot air at 60° C. for an hour so as to carry out polyhydric metal salt surface treatment, thereby obtaining a particulate water absorbing agent (10).

The aluminum sulfate treatment solution used was obtained by mixing 0.2 parts by mass of 50% sodium lactate aqueous solution (Musashino Chemical Laboratory, Ltd.) and 0.2 parts by mass of propyleneglycol with 2 parts by mass of tap water liquid aluminum sulfate 27 mass % solution (Asada Chemical Industry Co., Ltd.). Properties of the particulate water absorbing agent (10) are shown in Tables 2 and 3.

Example 11

The same operation as in Example 7 was carried out except that 74.29 g of 10% citric acid aqueous solution was used instead of 10.37 g of 50% malic acid aqueous solution, thereby obtaining a particulate water absorbing agent (11).

Example 12

The same operation as in Example 10 was carried out except that the particulate water absorbing agent (11) of Example 11 was used instead of the particulate water absorbing agent (10), thereby obtaining a particulate water absorbing agent (12).

Comparative Example 4

In accordance with Example 2 described in International Publication No. 2005/012369 pamphlet, a comparative particulate water absorbing agent (4) was obtained.

TABLE 1

|  | Particulate water absorbing agent (1) | Particulate water absorbing agent (2) | Comparative particulate water absorbing agent (1) | Comparative particulate water absorbing agent (2) |
|---|---|---|---|---|
| GVs(g/g) | 30 | 28 | 32 | 46 |
| AAP(g/g) | 20 | 25 | 20 | 10 |
| SFC($10^{-7} \cdot cm^3 \cdot s \cdot g^{-1}$) | 20 | 30 | 18 | 0 |
| D50(μm) | 480 | 390 | 410 | 350 |
| σζ | 0.38 | 0.35 | 0.34 | 0.38 |
| 150 μm pass (mass %) | 3 | 2 | 6 | 14 |
| Yellow Index before Exposure | 5 | 5.5 | 5.2 | 5.5 |
| Yellow Index after Exposure | 5.8 | 7.6 | 44.1 | 45.4 |
| Yellow Index Change rate | 116 | 138.2 | 848.1 | 825.5 |

TABLE 2

|  |  | Example 3 Particulate water absorbing agent (3) | Example 4 Particulate water absorbing agent (4) | Comparative Example 3 Comparative particulate water absorbing agent (3) | Comparative Example 4 Comparative particulate water absorbing agent (4) | Comparative Example 5 Particulate water absorbing agent (5) | Comparative Example 6 Particulate water absorbing agent (6) |
|---|---|---|---|---|---|---|---|
| GVs (g/g) | | 33 | 34 | 33 | 50 | 32 | 32 |
| pH-Extr. (%) | | 7.5 | 8.0 | 8.8 | — | 4.8 | 4.8 |
| AAP (g/g) | | — | — | — | 10 | — | — |
| SFC ($10^{-7} \cdot cm^3 \cdot s \cdot g^{-1}$) | | — | — | — | 0 | — | — |
| D50 (μm) | | — | — | — | 370 | 305 | 305 |
| σζ | | — | — | — | — | 0.35 | 0.35 |
| 150 μm pass (mass %) | | 0 | 0 | 0 | 13 | 2 | 2 |
| Coloring evaluation before | L | 90.64 | 90.96 | 90.92 | 90.92 | 90.16 | 90.16 |
|  | a | −0.58 | −0.57 | −0.61 | −0.61 | −0.43 | −0.43 |
|  | b | 6.16 | 6.15 | 4.34 | 4.34 | 6.52 | 6.52 |

TABLE 2-continued

|  |  | Example 3 Particulate water absorbing agent (3) | Example 4 Particulate water absorbing agent (4) | Comparative Example 3 Comparative particulate water absorbing agent (3) | Comparative Example 4 Comparative particulate water absorbing agent (4) | Comparative Example 5 Particulate water absorbing agent (5) | Comparative Example 6 Particulate water absorbing agent (6) |
|---|---|---|---|---|---|---|---|
| Exposure | YI | 11.9 | 11.8 | 8.3 | 8.3 | 12.8 | 12.8 |
| Coloring | L | 78.3 | 81.57 | 68.5 | 68.5 | 77.96 | 80.02 |
| evaluation | a | 2.05 | 1.49 | 3.57 | 3.57 | 1.62 | 1.32 |
| after | b | 9.95 | 8.89 | 14.94 | 14.94 | 9.73 | 8.53 |
| Exposure | YI | 24.81 | 21.0 | 43.0 | 43.0 | 24.0 | 22.0 |

TABLE 3

|  |  | Example 7 Particulate water absorbing agent (7) | Example 8 Particulate water absorbing agent (8) | Example 9 Particulate water absorbing agent (9) | Example 10 Particulate water absorbing agent (10) | Example 11 Particulate water absorbing agent (11) | Example 12 Particulate water absorbing agent (12) |
|---|---|---|---|---|---|---|---|
| GVs (g/g) | | 33 | 34 | 26.6 | 26.8 | 32 | 28.8 |
| pH-Extr. (%) | | 7.0 | 7.5 | — | — | 4.8 | — |
| AAP (g/g) | | — | — | 23.5 | 23.3 | — | 23.3 |
| SFC ($10^{-7} \cdot cm^3 \cdot s \cdot g^{-1}$) | | — | — | 115 | 130 | — | 130 |
| D50 (μm) | | 300 | 305 | — | — | 305 | — |
| σζ | | 0.35 | 0.35 | — | — | 0.35 | — |
| 150 μm pass (mass %) | | 2 | 2 | — | — | — | — |
| Coloring | L | 91.03 | 90.63 | 90.20 | 90.40 | 90.16 | 88.99 |
| evaluation | a | −0.27 | −0.75 | −0.15 | −0.16 | −0.43 | −0.15 |
| before | b | 4.38 | 5.36 | 5.45 | 5.25 | 6.52 | 5.25 |
| Exposure | YI | 8.6 | 10.2 | 10.9 | 10.5 | 12.8 | 11.1 |
| Coloring | L | 74.77 | 72.04 | 73.02 | 72.2 | 78.96 | 72.56 |
| evaluation | a | 2.42 | 2.81 | 2.19 | 2.1 | 1.62 | 2.5 |
| after Exposure | b | 12.85 | 13.41 | 11.11 | 12.01 | 9.73 | 12.56 |
|  | YI | 33.3 | 36.3 | 33.3 | 34.2 | 24.0 | 35.1 |

According to the particulate water absorbing agent of the present invention, it is possible to exhibit excellent absorbing ability (excellent permeability, a smaller amount of residual monomer, and excellent property for preventing the particulate water absorbing agent from being colored) unlike the conventional arts in case of using a highly concentrated water absorbent resin at the time of practical use in an absorbing article such as a diaper.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

In case of using the particulate water absorbing agent obtained by the present invention for a thin absorbent core of a diaper or the like with its concentration high, it is possible to provide an absorbent core whose absorbing performance is much more excellent, particularly, liquid permeability is much more excellent than a conventional absorbing agent and which is less likely to be colored and has excellent storage stability.

The invention claimed is:

1. A particulate water absorbing agent, comprising:
    a polyacrylic acid and/or a salt thereof water absorbent resin as a main component,
    wherein the water absorbent resin is polymerized from a monomer solution comprising an acrylic acid monomer and 10-200 ppm of a methoxyphenol by mass with respect to the acrylic acid monomer, and
    wherein the water absorbent resin internally includes:
        an aliphatic α-hydroxycarboxylic acid and/or a salt thereof, and
        an aminocarboxylic acid or aminophosphate metallic chelating agent, and
    wherein the water absorbent resin satisfies the following condition (a),
        (a) an amount of particles whose particle diameter is less than 150 μm ranges from 0 to 5 mass %, and a mass average particle diameter (D50) ranges from 200 to 600 μm, and a particle size distribution logarithmic standard deviation (σζ) ranges from 0.20 to 0.40.

2. The particulate water absorbing agent as set forth in claim 1, wherein the water absorbent resin satisfies at least one of the following conditions (b) and (c),
    (b) an absorbency against pressure (AAP) of the water absorbent resin with respect to 0.90 mass % of sodium chloride aqueous solution for 60 minutes is at least 15 g/g where the pressure is 4.8 kPa, and
    (c) a saline flow conductivity (SFC) is at least 5($\times 10^{-7} \cdot cm3 \cdot s \cdot g^{-1}$) where the saline is 0.69 mass % of sodium chloride aqueous solution.

3. The particulate water absorbing agent as set forth in claim 1, wherein a total amount of the aliphatic α-hydroxycarboxylic acid and/or a salt thereof ranges from 0.1 to 5 parts by weight with respect to 100 parts by weight of the water absorbent resin.

4. The particulate water absorbing agent as set forth in claim 1, wherein the aliphatic α-hydroxycarboxylic acid and/or a salt thereof is α-hydroxy polyhydric carboxylic acid and/or a salt thereof.

5. The particulate water absorbing agent as set forth in claim 1, wherein the water absorbent resin further includes polyhydric metal salt other than the aliphatic α-hydroxycarboxylic acid and/or a salt thereof.

6. An absorbing article, comprising the particulate water absorbing agent as set forth in claim 1 wherein the absorbing article absorbs urine, feces, and blood.

7. A method for producing a particulate water absorbing agent including a polyacrylic acid and/or a salt thereof water absorbent resin as a main component, said method comprising the steps of:
(a) cross-linking and polymerizing a monomer solution containing acrylic acid and/or a salt thereof as a main component and 10-200 ppm of a methoxyphenol by mass with respect to the acrylic acid;
(b) drying a hydrogel polymer obtained by the polymerization to produce the water absorbent resin; and
(c) classifying the water absorbent resin to produce the particulate water absorbing agent;
wherein the polymerization is carried out in the presence of an aliphatic α-hydroxycarboxylic acid and/or a salt thereof and an aminocarboxylic acid or aminophosphate metallic chelating agent used together;
and wherein the particulate water absorbing agent comprises an amount of particles whose particle diameter is less than 150 μm ranges from 0 to 5 mass %, and a mass average particle diameter (D50) ranges from 200 to 600 μm, and a particle size distribution logarithmic standard deviation (σζ) ranges from 0.20 to 0.40.

8. The method as set forth in claim 7, wherein the aliphatic α-hydroxycarboxylic acid and/or a salt thereof is α-hydroxy polyhydric carboxylic acid and/or a salt thereof.

9. The method as set forth in claim 8, wherein a total amount of the aliphatic α-hydroxycarboxylic acid and/or a salt thereof ranges from 0.1 to 5 parts by weight with respect to 100 parts by weight of the water absorbent resin.

10. The method as set forth in claim 7, further comprising the step of cross-linking a surface of the water absorbent resin having been dried.

11. The method as set forth in claim 7, wherein polyhydric metal salt other than the aliphatic α-hydroxycarboxylic acid and/or a salt thereof is further added to the water absorbent resin.

12. A method for producing a particulate water absorbing agent including a polyacrylic acid and/or a salt thereof water absorbent resin as a main component, said method comprising the steps of:
(a) cross-linking and polymerizing a monomer solution containing acrylic acid and/or a salt thereof as a main component and 10-200 ppm of a methoxyphenol by mass with respect to the acrylic acid;
(b) drying a hydrogel polymer obtained by the polymerization to produce the water absorbent resin; and
(c) classifying the water absorbent resin to produce the particulate water absorbing agent;
wherein an aliphatic α-hydroxycarboxylic acid and/or a salt thereof and an aminocarboxylic acid or aminophosphate metallic chelating agent are added together to the hydrogel cross-linked polymer after the polymerization;
and wherein the particulate water absorbing agent comprises an amount of particles whose particle diameter is less than 150 μm ranges from 0 to 5 mass %, and a mass average particle diameter (D50) ranges from 200 to 600 μm, and a particle size distribution logarithmic standard deviation (σζ) ranges from 0.20 to 0.40.

13. The method as set forth in claim 12, wherein the aliphatic α-hydroxycarboxylic acid and/or a salt thereof is α-hydroxy polyhydric carboxylic acid and/or a salt thereof.

14. The method as set forth in claim 13, wherein a total amount of the aliphatic α-hydroxycarboxylic acid and/or a salt thereof ranges from 0.1 to 5 parts by weight with respect to 100 parts by weight of the water absorbent resin.

15. The method as set forth in claim 12, further comprising the step of cross-linking a surface of the water absorbent resin having been dried.

16. The method as set forth in claim 12, wherein polyhydric metal salt other than the aliphatic α-hydroxycarboxylic acid and/or a salt thereof is further added to the water absorbent resin.

17. A method for producing a particulate water absorbing agent including a polyacrylic acid and/or a salt thereof, water absorbent resin as a main component, said method comprising the steps of:
(a) cross-linking and polymerizing a monomer solution containing acrylic acid and/or a salt thereof as a main component and 10-200 ppm of a methoxyphenol by mass with respect to the acrylic acid; and
(b) drying a hydrogel polymer obtained by the polymerization to produce the water absorbent resin; and
(c) classifying the water absorbent resin to produce the particulate water absorbing agent;
wherein an aliphatic α-hydroxycarboxylic acid and/or a salt thereof and an aminocarboxylic acid or aminophosphate metallic chelating agent are added together to the monomer aqueous solution during the polymerization; and
wherein the particulate water absorbing agent comprises an amount of particles whose particle diameter is less than 150 μm ranges from 0 to 5 mass %, and a mass average particle diameter (D50) ranges from 200 to 600 μm, and a particle size distribution logarithmic standard deviation (σζ) ranges from 0.20 to 0.40.

18. The method as set forth in claim 17, wherein the aliphatic α-hydroxycarboxylic acid and/or a salt thereof is α-hydroxy polyhydric carboxylic acid and/or a salt thereof.

19. The method as set forth in claim 18, wherein a total amount of the aliphatic α-hydroxycarboxylic acid and/or a salt thereof ranges from 0.1 to 5 parts by weight with respect to 100 parts by weight of the water absorbent resin.

20. The method as set forth in claim 17, further comprising the step of cross-linking a surface of the water absorbent resin having been dried.

21. The method as set forth in claim 17, wherein polyhydric metal salt other than the aliphatic α-hydroxycarboxylic acid and/or a salt thereof is further added to the water absorbent resin.

* * * * *